US010166224B2

(12) United States Patent
Myers et al.

(10) Patent No.: US 10,166,224 B2
(45) Date of Patent: *Jan. 1, 2019

(54) NICOTINE SALT WITH META-SALICYLIC ACID AND APPLICATIONS THEREIN

(71) Applicant: Alexza Pharmaceuticals, Inc., Mountain View, CA (US)

(72) Inventors: Daniel J. Myers, Mountain View, CA (US); James Cassella, Essex, CT (US)

(73) Assignee: ALEXZA PHARMACEUTICALS, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,129

(22) Filed: Aug. 7, 2017

(65) Prior Publication Data
US 2018/0021328 A1 Jan. 25, 2018

Related U.S. Application Data

(63) Continuation of application No. 14/904,359, filed as application No. PCT/US2014/046288 on Jul. 11, 2014, now Pat. No. 9,724,341.

(60) Provisional application No. 62/020,766, filed on Jul. 3, 2014, provisional application No. 61/845,333, filed on Jul. 11, 2013.

(51) Int. Cl.
| | |
|---|---|
| *A24B 15/16* | (2006.01) |
| *A61K 31/60* | (2006.01) |
| *A61K 31/465* | (2006.01) |
| *A61M 15/06* | (2006.01) |
| *A61K 9/00* | (2006.01) |
| *A61M 5/00* | (2006.01) |
| *A61M 11/04* | (2006.01) |
| *A61M 15/00* | (2006.01) |
| *A61M 35/00* | (2006.01) |
| *A61M 37/00* | (2006.01) |
| *C07D 401/04* | (2006.01) |
| *C07C 63/08* | (2006.01) |
| *H05B 1/02* | (2006.01) |
| *A24F 47/00* | (2006.01) |
| *C07C 65/10* | (2006.01) |
| *A61K 9/70* | (2006.01) |
| *A61M 11/00* | (2006.01) |
| *A61M 16/00* | (2006.01) |

(52) U.S. Cl.
CPC .......... *A61K 31/465* (2013.01); *A24B 15/167* (2016.11); *A24F 47/002* (2013.01); *A61K 9/0004* (2013.01); *A61K 9/007* (2013.01); *A61K 31/60* (2013.01); *A61M 5/00* (2013.01); *A61M 11/041* (2013.01); *A61M 15/0065* (2013.01); *A61M 15/0081* (2014.02); *A61M 15/0083* (2014.02); *A61M 15/06* (2013.01); *A61M 35/00* (2013.01); *A61M 37/00* (2013.01); *C07C 63/08* (2013.01); *C07C 65/10* (2013.01); *C07D 401/04* (2013.01); *H05B 1/025* (2013.01); *A61K 9/7007* (2013.01); *A61M 11/001* (2014.02); *A61M 11/042* (2014.02); *A61M 11/047* (2014.02); *A61M 15/002* (2014.02); *A61M 15/0066* (2014.02); *A61M 2016/0015* (2013.01); *A61M 2205/276* (2013.01); *A61M 2205/3368* (2013.01); *A61M 2205/3553* (2013.01); *A61M 2205/3569* (2013.01); *A61M 2205/3576* (2013.01); *A61M 2205/3584* (2013.01); *A61M 2205/3592* (2013.01); *A61M 2205/364* (2013.01); *A61M 2205/368* (2013.01); *A61M 2205/3653* (2013.01); *A61M 2205/50* (2013.01); *A61M 2205/52* (2013.01); *A61M 2205/8206* (2013.01); *A61M 2209/06* (2013.01); *A61M 2230/06* (2013.01); *A61M 2230/205* (2013.01); *A61M 2230/30* (2013.01); *A61M 2230/42* (2013.01); *C07C 2601/16* (2017.05)

(58) Field of Classification Search
CPC .... A24B 15/167; A61K 31/60; A61K 31/465; A61B 15/167
See application file for complete search history.

(56) References Cited

U.S. PATENT DOCUMENTS

| | | |
|---|---|---|
| 4,284,089 A | 8/1981 | Ray |
| 6,682,716 B2 | 1/2004 | Hodges et al. |
| 6,716,415 B2 | 4/2004 | Rabinowitz et al. |
| 6,716,416 B2 | 4/2004 | Rabinowitz et al. |

(Continued)

FOREIGN PATENT DOCUMENTS

| | | |
|---|---|---|
| CN | 101068784 A | 11/2007 |
| CN | 101437496 A | 5/2009 |

(Continued)

OTHER PUBLICATIONS

U.S. Appl. No. 13/311,660, filed Dec. 6, 2011, Bennett et al.

(Continued)

*Primary Examiner* — Theodore R. West
(74) *Attorney, Agent, or Firm* — Adsero IP

(57) ABSTRACT

The present disclosure relates generally to the field of nicotine delivery. The disclosure teaches a nicotine meta-salicylate. More specifically, the disclosure teaches a condensation nicotine aerosol where nicotine meta-salicylate is vaporized. This disclosure relates to aerosol nicotine delivery devices. The delivery devices can be activated by actuation mechanisms to vaporize thin films comprising a nicotine meta-salicylate. More particularly, this disclosure relates to thin films of nicotine salt with meta salicylic acid for the treatment of nicotine craving and for effecting smoking cessation.

3 Claims, 19 Drawing Sheets

(56) References Cited

U.S. PATENT DOCUMENTS

| | | |
|---|---|---|
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,776,978 B2 | 8/2004 | Rabinowitz et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,387,788 B1 | 6/2008 | Carrara et al. |
| 7,402,777 B2 | 7/2008 | Hale et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,459,469 B2 | 12/2008 | Munoz et al. |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,494,344 B2 | 2/2009 | Galauner et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 | 9/2009 | Hale et al. |
| 7,601,337 B2 | 10/2009 | Rabinowitz et al. |
| 7,645,442 B2 | 1/2010 | Hale et al. |
| 7,766,013 B2 | 8/2010 | Wensley et al. |
| 7,834,295 B2 | 11/2010 | Sharma et al. |
| 7,913,688 B2 | 3/2011 | Cross et al. |
| 7,923,662 B2 | 4/2011 | Hale et al. |
| 7,942,147 B2 | 5/2011 | Hodges et al. |
| 7,981,401 B2 | 7/2011 | Every et al. |
| 7,987,846 B2 | 8/2011 | Hale et al. |
| 7,988,952 B2 | 8/2011 | Rabinowitz et al. |
| 8,003,080 B2 | 8/2011 | Rabinowitz et al. |
| 8,074,644 B2 | 12/2011 | Hale et al. |
| 8,173,107 B2 | 5/2012 | Rabinowitz et al. |
| 8,235,037 B2 | 8/2012 | Hale et al. |
| 8,288,372 B2 | 10/2012 | Hale et al. |
| 8,333,197 B2 | 12/2012 | Cross et al. |
| 8,387,612 B2 | 3/2013 | Damani et al. |
| 8,506,935 B2 | 8/2013 | Hale et al. |
| 8,955,512 B2 | 2/2015 | Hales et al. |
| 8,991,387 B2 | 3/2015 | Damani et al. |
| 9,211,382 B2 | 12/2015 | Hale et al. |
| 9,439,907 B2 | 9/2016 | Hale et al. |
| 9,440,034 B2 | 9/2016 | Hale et al. |
| 9,687,487 B2 | 6/2017 | Hodges et al. |
| 9,724,341 B2 * | 8/2017 | Myers .................. A61K 9/0004 |
| 2003/0032638 A1 | 2/2003 | Kim et al. |
| 2003/0051728 A1 | 3/2003 | Lloyd et al. |
| 2003/0118512 A1 | 6/2003 | Shen |
| 2003/0131843 A1 | 7/2003 | Lu |
| 2003/0138508 A1 | 7/2003 | Novack et al. |
| 2004/0096402 A1 | 5/2004 | Hodges et al. |
| 2004/0101481 A1 | 5/2004 | Hale et al. |
| 2004/0105818 A1 | 6/2004 | Every et al. |
| 2004/0191322 A1 | 9/2004 | Hansson |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2006/0032496 A1 | 2/2006 | Hale et al. |
| 2006/0120962 A1 | 6/2006 | Rabinowitz et al. |
| 2006/0193788 A1 | 8/2006 | Hale et al. |
| 2006/0257329 A1 | 11/2006 | Rabinowitz et al. |
| 2007/0122353 A1 | 5/2007 | Hale et al. |
| 2007/0286816 A1 | 12/2007 | Hale et al. |
| 2008/0038363 A1 | 2/2008 | Zaffaroni et al. |
| 2008/0216828 A1 | 9/2008 | Wensley et al. |
| 2008/0299048 A1 | 12/2008 | Hale et al. |
| 2008/0306285 A1 | 12/2008 | Hale et al. |
| 2008/0311176 A1 * | 12/2008 | Hale .................... A61K 9/0004 424/443 |
| 2009/0062254 A1 | 3/2009 | Hale et al. |
| 2009/0180968 A1 | 7/2009 | Hale et al. |
| 2010/0006092 A1 | 1/2010 | Hale et al. |
| 2010/0055048 A1 | 3/2010 | Hale et al. |
| 2010/0065052 A1 | 3/2010 | Sharma et al. |

(56) References Cited

U.S. PATENT DOCUMENTS

| | | |
|---|---|---|
| 2010/0068155 A1 | 3/2010 | Lei et al. |
| 2010/0181387 A1 | 7/2010 | Zaffaroni et al. |
| 2010/0294268 A1 | 11/2010 | Wensley et al. |
| 2010/0300433 A1 | 12/2010 | Sharma et al. |
| 2011/0233043 A1 | 9/2011 | Cross et al. |
| 2011/0240013 A1 | 10/2011 | Hale et al. |
| 2011/0240014 A1 | 10/2011 | Bennett et al. |
| 2011/0240022 A1 | 10/2011 | Hodges et al. |
| 2011/0244020 A1 | 10/2011 | Hale et al. |
| 2011/0245493 A1 | 10/2011 | Rabinowitz et al. |
| 2011/0253135 A1 | 10/2011 | Hale et al. |
| 2012/0048963 A1 | 3/2012 | Sharma et al. |
| 2013/0032139 A1 | 2/2013 | Hale et al. |
| 2013/0078307 A1 | 3/2013 | Holton et al. |
| 2013/0180525 A1 | 7/2013 | Cross et al. |
| 2014/0060525 A1 | 3/2014 | Hale et al. |
| 2014/0060532 A1 | 3/2014 | Hodges et al. |
| 2014/0066618 A1 | 3/2014 | Hale et al. |
| 2014/0072605 A1 | 3/2014 | Bennett et al. |
| 2015/0157635 A1 | 6/2015 | Hale et al. |
| 2015/0250800 A1 | 9/2015 | Hale et al. |
| 2015/0265783 A1 | 9/2015 | Damani et al. |
| 2016/0166564 A1 | 6/2016 | Myers et al. |
| 2016/0324845 A1 | 11/2016 | Myers et al. |
| 2016/0374937 A1 | 12/2016 | Hale et al. |
| 2017/0049974 A1 | 2/2017 | Wensley et al. |
| 2017/0105246 A1 | 4/2017 | Cross et al. |
| 2017/0281884 A1 | 10/2017 | Hodges et al. |
| 2018/0021328 A1 | 1/2018 | Myers et al. |
| 2018/0126098 A1 | 5/2018 | Sharma et al. |

FOREIGN PATENT DOCUMENTS

| | | |
|---|---|---|
| EP | 1578422 B1 | 6/2007 |
| JP | 2004149447 | 5/2004 |
| JP | 2006-511566 | 4/2006 |
| JP | 2008-519766 | 6/2008 |
| JP | 2008-519768 | 6/2008 |
| JP | 2010-525354 | 7/2010 |
| WO | WO 2004/056363 | 7/2004 |
| WO | WO 2006/053039 | 5/2006 |
| WO | WO 2007/104575 | 9/2007 |
| WO | WO 2009/037319 | 3/2009 |
| WO | WO 2013/043866 | 3/2013 |
| WO | WO 2015/006652 | 1/2015 |

OTHER PUBLICATIONS

U.S. Appl. No. 13/597,865, filed Aug. 29, 2012, Bennett et al.
European Search report for Application No. 14822991.7, dated Dec. 7, 2016, 8 pages.
International Preliminary Report on Patentability for PCT/US2014/046288 dated Jan. 21, 2016, 9 pages.
International Search Report and Written Opinion for PCT/US2014/046288 dated Oct. 2, 2014, 9 pages.
Office Action for Application No. 2016-525796, dated Mar. 26, 2018, 2 pages (English Translation).
Office Action for Application No. 2016-525796, dated Mar. 26, 2018, 2 pages (Untranslated).
Office Action for Application No. 201480050267.X, dated Jan. 30, 2018, 4 pages (English Translation).
Office Action for Application No. 201480050267.X, dated Jan. 30, 2018, 10 pages (Untranslated).
Kexun Xu, "Handbook of Organic Chemical Material and Intermediates", Dec. 31, 1989, pp. 490-491.
Office action for Application No. 2,918,145, dated Mar. 24, 2017, 4 pages.

* cited by examiner ortho-salicylic acid para-salicylic acid 3-hydroxybenzoic acid
meta-salicylic acid ortho isomer para isomer meta isomer

NICOTINE SALT WITH META-SALICYLIC ACID AND APPLICATIONS THEREIN

RELATED APPLICATIONS

This application is a continuation of U.S. application Ser. No. 14/904,359, filed Jan. 11, 2016, entitled "Nicotine Salt with Meta-Salicylic Acid and Applications Therein", which application claims priority to PCT/US2014/046288, filed Jul. 11, 2014, entitled "Nicotine Salt with Meta-Salicylic Acid and Applications", which application claims priority to U.S. provisional application Ser. No. 61/845,333 entitled "Nicotine Salt with Meta-Salicylic Acid," filed Jul. 11, 2013, Myers and application claims priority to U.S. provisional application Ser. No. 62/020,766 entitled "Drug Delivery and Cessation System, Apparatus, and Method," filed Jul. 3, 2014, Cassella. The entire disclosures of which are hereby incorporated by reference. Any disclaimer that may have occurred during the prosecution of the above-referenced applications is hereby expressly rescinded, and reconsideration of all relevant art is respectfully requested.

TECHNICAL FIELD

The present disclosure relates generally to the field of nicotine delivery. The disclosure teaches a nicotine meta-salicylate. More specifically, the disclosure teaches a condensation nicotine aerosol where nicotine meta-salicylate is vaporized. This disclosure relates to aerosol nicotine delivery devices. The delivery devices can be activated by actuation mechanisms to vaporize thin films comprising a nicotine meta-salicylate. More particularly, this disclosure relates to thin films of nicotine meta-salicylate for the treatment of nicotine craving and for effecting smoking cessation. The disclosure also relates to methods, systems, apparatuses, and computer software for delivering dosages of a drug to a user, and for drug cessation control, and, more particularly to methods, systems, apparatuses, and computer software for delivering dosages of nicotine to a user, and for nicotine cessation control.

BACKGROUND

Cigarette smoking provides an initial sharp rise in nicotine blood level as nicotine is absorbed through the lungs of a smoker. In general, a blood level peak produced by cigarettes of between 30-40 ng/mL is attained within 10 minutes of smoking. (Hukkanen et al., Am Soc. Pharm Exp Therapy 2013) The rapid rise in nicotine blood level is postulated to be responsible for the postsynaptic effects at nicotinic cholinergic receptors in the central nervous system and at autonomic ganglia which induces the symptoms experienced by cigarette smokers, and may also be responsible for the craving symptoms associated with cessation of smoking.

While many nicotine replacement therapies have been developed, none of the therapies appear to reproduce the pharmacokinetic profile of the systemic nicotine blood concentration provided by cigarettes. As a consequence, conventional nicotine replacement therapies have not proven to be particularly effective in enabling persons to quit smoking. For example, many commercially available products for nicotine replacement in smoking cessation therapy are intended to provide a stable baseline concentration of nicotine in the blood. Nicotine chewing gum and transdermal nicotine patches are two examples of smoking cessation products which, while providing blood concentrations of nicotine similar to that provided by cigarettes at times greater than about 30 minutes, do not reproduce the sharp initial rise in blood nicotine concentrations obtained by smoking cigarettes. Nicotine gum is an ion-exchange resin that releases nicotine slowly when a patient chews, and the nicotine present in the mouth is delivered to the systemic circulation by buccal absorption. Nicotine patches provide a consistent, steady release rate, which leads to low, stable blood levels of nicotine. Thus, both nicotine gum and transdermal nicotine do not reproduce the pharmacokinetic profile of nicotine blood levels obtained through cigarette smoking, and thus do not satisfy the craving symptoms experienced by many smokers when attempting to quit smoking.

Inhalation products which generate nicotine vapor are also ineffective as inhaled vapors are predominately absorbed through the tongue, mouth and throat, and are not deposited into the lungs. Smokeless nicotine products such as chewing tobacco, oral snuff or tobacco sachets deliver nicotine to the buccal mucosa where, as with nicotine gum, the released nicotine is absorbed only slowly and inefficiently. Nicotine blood levels from these products require approximately 30 minutes of use to attain a maximum nicotine blood concentration of approximately 12 ng/mL, which is less than half the peak value obtained from smoking one cigarette. Low nicotine blood levels obtained using a buccal absorption route may be due to first pass liver metabolism. Orally administered formulations and lozenges are also relatively ineffective.

Rapid vaporization of thin films of drugs at temperatures up to 600° C. in less than 500 msec in an air flow can produce drug aerosols having high yield and high purity with minimal degradation of the drug. Condensation drug aerosols can be used for effective pulmonary delivery of drugs using inhalation medical devices. Devices and methods in which thin films of drugs deposited on metal substrates are vaporized by electrically resistive heating have been demonstrated. Chemically-based heat packages which can include a fuel capable of undergoing an exothermic metal oxidation-reduction reaction within an enclosure can also be used to produce a rapid thermal impulse capable of vaporizing thin films to produce high purity aerosols, as disclosed, for example in U.S. application Ser. No. 10/850,895 entitled "Self-Contained heating Unit and Drug-Supply Unit Employing Same" filed May 20, 2004, and U.S. application Ser. No. 10/851,883, entitled "Percussively Ignited or Electrically Ignited Self-Contained Heating Unit and Drug Supply Unit Employing Same," filed May 20, 2004, the entirety of both of which are herein incorporated by reference. These devices and methods are appropriate for use with compounds that can be deposited as physically and chemically stable solids. Unless vaporized shortly after being deposited on the metal surface, liquids can evaporate or migrate from the surface. Therefore, while such devices can be used to vaporize liquids, the use of liquid drugs can impose certain undesirable complexity. Nicotine is a liquid at room temperature with a relatively high vapor pressure. Therefore, known devices and methods are not particularly suited for producing nicotine aerosols using the liquid drug.

It is postulated that treatment of nicotine craving and smoking cessation can be addressed by treatment regimens and/or therapies that reproduce the rapid onset of high nicotine blood concentrations achieved during cigarette smoking. A cigarette smoker typically inhales about 10 times over a period of about 5 minutes. Therefore, a nicotine delivery device capable of simulating the use profile of cigarette smoking can include from 5 to 20 doses of up to about 200 μg each of nicotine, which could then be intermittently released upon request by the user.

Thus, there remains a need for a nicotine replacement therapy that provides a pharmacokinetic profile similar to that obtained by cigarette smoking, and thereby directly addresses the craving symptoms associated with the cessation of smoking.

SUMMARY OF THE EMBODIMENTS

Accordingly, one aspect of the present disclosure teaches nicotine meta-salicylate. One aspect of the present disclosure provides a compound comprising a volatile nicotine meta-salicylate compound, wherein the compound is selectively vaporizable when heated.

One aspect of the present disclosure provides a nicotine delivery device comprising an electric multidose platform (EMD) as shown in FIG. 13.

One aspect of the present disclosure provides a nicotine delivery device comprising a housing defining an airway, wherein the airway comprises at least one air inlet and a mouthpiece having at least one air outlet, at least one heat package disposed within the airway, at least nicotine meta-salicylate disposed on the at least one heat package, and a mechanism configured to actuate the at least one heat package.

One aspect of the present disclosure provides a nicotine delivery device comprising a housing defining an airway, wherein the airway comprises at least one air inlet and a mouthpiece having at least one air outlet, at least one percussively activated heat package disposed within the airway, at least nicotine meta-salicylate disposed on the at least one percussively activated heat package, and a mechanism configured to impact the at least one percussively activated heat package. For purpose of clarity, "percussively activated heat package" herein means a heat package that has been configured so that it can be fired or activated by percussion. An "unactivated heat package" or "non-activated heat package" refers herein to a percussively activated heat package in a device, but one that is not yet positioned in the device so that it can be directly impacted and fired, although the heat package itself is configured to be activated by percussion when so positioned.

One aspect of the present disclosure provides a method of producing an aerosol of nicotine by selectively vaporizing the compound from a thin film comprising nicotine meta-salicylate.

One aspect of the present disclosure provides a method of delivering nicotine to a person comprising providing a nicotine delivery device comprising, a housing defining an airway, wherein the airway comprises at least one air inlet and a mouthpiece having at least one air outlet, at least two or more heat packages disposed within the airway, at least nicotine meta-salicylate disposed on the heat packages, and a mechanism configured to activate heat packages, inhaling through the mouthpiece, and activating the heat package, wherein the activated heat package vaporizes the at least nicotine meta-salicylate to form an aerosol comprising the nicotine in the airway which is inhaled by the person.

One aspect of the present disclosure provides a method for treating nicotine craving and smoking cessation using a nicotine aerosol.

One aspect of the present disclosure provides for tapering of the nicotine dose through behavior modification therapy, utilizing electronic dose controlling and/or tapering through dose reduction.

It is to be understood that both the foregoing general description and the following detailed description are exemplary and explanatory only and are not restrictive of certain embodiments, as claimed.

The present invention relates to methods of manufacture and compositions which facilitate the inhalation delivery of nicotine to a patient for use as either a smoking substitute, an aid to smoking cessation, or, as will be discussed later, in the treatment of illnesses. One embodiment of the present disclosure is capable of delivering nicotine into a patient's blood in a manner which results in attainment of blood nicotine concentrations similar to the blood nicotine concentrations attained through smoking cigarettes to thereby address the physical cravings for nicotine which a smoker develops. In addition, the nicotine-containing dosage form disclosed provides a patient the opportunity, if desired, for physical manipulation and oral stimulation associated with repeated insertion and removal of the dosage form into and out of the patient's mouth to thereby address some of the psychological cravings which a smoker develops.

It is one object of the present disclosure to provide a nicotine-containing dosage form which can be utilized as part of a long-term smoking cessation program. Another object is to provide a nicotine-containing dosage form which is suitable for use as a smoking substitute whenever smoking is not allowed or desired. A further object of the disclosure is to provide a nicotine aerosol highly free of the toxins present in cigarettes. A further object of the disclosure is to provide a nicotine-containing dosage form which can maintain nicotine plasma concentrations within a range which alleviates smoking withdrawal symptoms. Another object of the present disclosure is to provide a nicotine-containing dosage form which can provide nicotine plasma concentrations similar to those achieved by smoking a cigarette, including a similar pharmacological profile of nicotine delivery. Additionally, the disclosure teaches a nicotine-containing dosage form which addresses some of the psychological needs of an individual who desires to quit smoking. The disclosure also teaches a nicotine-containing dosage form which is easy to use in order to promote patient compliance. The disclosure further teaches the cessation/diminution of the craving for a cigarette by allowing the patient to self-titrate the amount of nicotine to overcome the person's individual craving.

The disclosure teaches a new nicotine salt, nicotine m-salicylate (nicotine meta-salicylate). It is noted that m-salicylic acid is also referred to as 3-hydroxybenzoic acid. In one aspect, the disclosure teaches a novel composition for delivery of nicotine comprising a condensation aerosol formed by volatilizing a heat stable nicotine meta-salicylate composition under conditions effective to produce a heated vapor of said nicotine meta-salicylate composition and condensing the heated vapor of the drug composition to form condensation aerosol particles, wherein said condensation aerosol particles are characterized by less than 10% nicotine degradation products, wherein the aerosol MMAD is less than 3 microns and wherein said heat stable nicotine meta-salicylate composition comprises nicotine meta-salicylate.

In some variations, the aerosol comprises at least 50% by weight of nicotine condensation particles. In other variations the aerosol comprises at least 90% or 95% by weight of the nicotine condensation particles. Similarly, in some variations, the aerosol is substantially free of thermal degradation products, and in some variations, the condensation aerosol has a MMAD in the range of 0.1-3 μm. In certain embodiments, the particles have an MMAD of less than 5 microns, preferably less than 3 microns. Preferably, the particles have a mass median aerodynamic diameter of from 0.2 to 5 microns, or most preferably from 0.2 to 3 microns. Typically, the aerosol comprises a therapeutically effective amount of nicotine and in some variations may comprise pharmaceutically acceptable excipients. In some variations, the carrier gas is air. In some variations, other gases or a combination of various gases may be used. In some variations, the percent of nicotine free base is at least 10%. In some variations, the percent of nicotine free base in the aerosol is at least 20%. In some variations, the percent of nicotine free base in the aerosol is at least 30%. In some variations, the percent of nicotine free base in the aerosol is at least 40%. In some variations, the percent of nicotine free base in the aerosol is at least 50%. In some variations, the percent of nicotine free base in the aerosol is between 1% and 10%. In some variations, the percent of nicotine free base in the aerosol is between 10% and 20%. In some variations, the percent of nicotine free base in the aerosol is between 20% and 30%. In some variations, the percent of nicotine free base in the aerosol is between 30% and 40%. In some variations, the percent of nicotine free base in the aerosol is between 40% and 50%.

In another aspect of the invention, the invention provides compositions for inhalation delivery, comprising an aerosol of vaporized nicotine condensed into particles, characterized by less than 5% drug degradation products, and wherein said aerosol has a mass median aerodynamic diameter between 0.1-3 microns.

In some variations of the aerosol compositions, the carrier gas is a non-propellant, non-organic solvent carrier gas. In some variations of the aerosol compositions, the carrier gas is air. In some variations, the aerosol is substantially free of organic solvents and propellants.

In other embodiments, aerosols of nicotine are provided that contain less than 5% nicotine degradation products, and a mixture of a carrier gas and condensation particles, formed by condensation of a vapor of nicotine in said carrier gas; wherein the MMAD of the aerosol increases over time, within the size range of 0.1 to 3 microns as said vapor cools by contact with the carrier gas.

In some variations, the aerosol comprises at least 50% by weight of nicotine condensation particles. In other variations the aerosol comprises at least 90% or 95% by weight of the nicotine condensation particles. In some variations, the MMAD of the aerosol is less than 2 microns and increases over time. In some variations, the carrier gas is air. In some variations, other gases or a combination of various gases may be used.

The condensation aerosols of the various embodiments are typically formed by preparing a film containing a nicotine meta-salicylate composition of a desired thickness on a heat-conductive and impermeable substrate and heating said substrate to vaporize said film, and cooling said vapor thereby producing aerosol particles containing said composition. Rapid heating in combination with the gas flow helps reduce the amount of decomposition. Thus, a heat source is used that typically heats the substrate to a temperature of greater than 200° C., preferably at least 250° C., more preferably at least 300° C. or 350° C. and produces substantially complete volatilization of the nicotine meta-salicylate composition from the substrate within a period of 2 seconds, preferably, within 1 second, and more preferably, within 0.5 seconds.

Typically, the gas flow rate over the vaporizing compound is between about 1 and 10 L/minute. Further, the gas flow rate over the vaporizing compound can be between about 2 and 8 L/minute.

The film thickness is such that an aerosol formed by vaporizing the nicotine meta-salicylate by heating the substrate and condensing the vaporized compound contains 10% by weight or less nicotine-degradation product. The use of thin films allows a more rapid rate of vaporization and hence, generally, less thermal nicotine degradation. Typically, the film has a thickness between 0.05 and 30 microns. In some variations, the film has a thickness between 0.5 and 25 microns. In some variations the film has a thickness of about 21 microns. The selected area of the substrate surface expanse is such as to yield an effective dose of the nicotine aerosol.

In a related aspect, the disclosure teaches kits for delivering a nicotine condensation aerosol that typically comprises a composition devoid of solvents and excipients and comprising a heat stable nicotine meta-salicylate, and a device for forming and delivering via inhalation a condensation aerosol. The device for forming a drug aerosol typically comprises an element configured to heat the composition to form a vapor, an element allowing the vapor to condense to form a condensation aerosol, and an element permitting a user to inhale the condensation aerosol. Typically, the element configured to heat the composition comprises a heat-conductive substrate and formed on the substrate is typically a nicotine meta-salicylate composition film containing an effective dose of nicotine when the nicotine is administered in an aerosol form. A heat source in the device is operable to supply heat to the substrate to produce a substrate temperature, typically that is greater than 300° C., to substantially volatilize the nicotine meta-salicylate composition film from the substrate in a period of 2 seconds or less, more preferably, in a period of 500 milliseconds or less. The device may further comprise features such as breath-actuation, lockout elements, dose counting/logging or tapering methods.

In yet another aspect, the disclosure teaches kits for delivering nicotine aerosol comprising a thin film of a nicotine meta-salicylate composition and a device for dispensing said film as a condensation aerosol. Typically, the film thickness is between 0.5 and 30 microns. The film can comprise pharmaceutically acceptable excipients and is typically heated at a rate so as to substantially volatilize the film in 500 milliseconds or less.

To achieve the foregoing objects, and in accordance with the invention as embodied and broadly described herein, a nicotine-containing dosage form is provided. The dosage form is configured having a nicotine-containing composition wherein the nicotine composition comprises nicotine meta-salicylate.

These and other objects and features of the invention will be more fully appreciated when the following detailed description of the invention is read in conjunction with the accompanying drawings.

Figure 1:
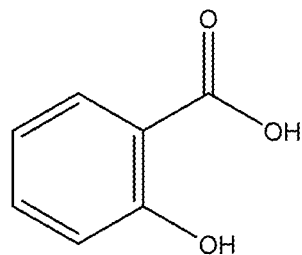
FIG. 1 is ortho-salicylic acid, para-salicylic acid and 3-hydroxybenzoic acid (meta-salicylic acid).
Figure 1:
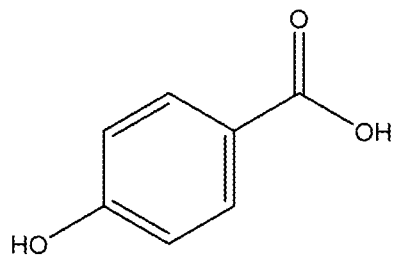
Figure 1:
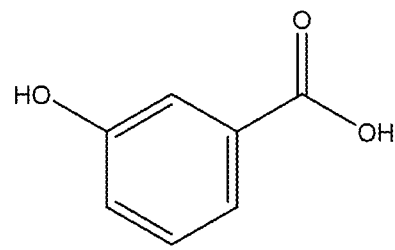

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DESCRIPTION OF VARIOUS EMBODIMENTS

Definitions

As defined herein, the following terms shall have the following meanings when reference is made to them throughout the specification.

"Aerodynamic diameter" of a given particle refers to the diameter of a spherical droplet with a density of 1 g/mL (the density of water) that has the same settling velocity as the given particle.

"Aerosol" refers to a collection of solid or liquid particles suspended in a gas.

"Aerosol mass concentration" refers to the mass of particulate matter per unit volume of aerosol.

"Condensation aerosol" refers to an aerosol that has been formed by the vaporization of a composition and subsequent cooling of the vapor, such that the vapor condenses to form particles.

"Decomposition index" refers to a number derived from an assay. The number is determined by subtracting the purity of the generated aerosol, expressed as a fraction, from 1.

"Drug" means any substance that is used in the prevention, diagnosis, alleviation, treatment or cure of a condition. The drug is preferably in a form suitable for thermal vapor delivery, such as an ester, free acid, or free base form. The terms "drug", "compound", and "medication" are used herein interchangeably. As described in throughout the specification, the term drug includes nicotine and nicotine meta-salicylate.

"Drug composition" refers to a composition that comprises only pure drug, two or more drugs in combination, or one or more drugs in combination with additional components. Additional components can include, for example, pharmaceutically acceptable excipients, carriers, and surfactants.

"Drug degradation product" or "thermal degradation product" are used interchangeably and means any byproduct, which results from heating the drug(s) and is not responsible for producing a therapeutic effect.

"Drug supply article" or "drug supply unit" are used interchangeably and refers to a substrate with at least a portion of its surface coated with one or more drug compositions. Drug supply articles of the invention may also include additional elements such as, for example, but not limitation, a heating element.

"Effective amount of nicotine" means the amount of nicotine required to achieve the effect achieved from nicotine through smoking cigarettes. The effect could be any effect ranging from symptom amelioration with regard to withdraw to symptom treatment. In one embodiment, the effective amount of nicotine is between 50 to 200 µg/dose.

"Fraction drug degradation product" refers to the quantity of drug degradation products present in the aerosol particles divided by the quantity of drug plus drug degradation product present in the aerosol, i.e. (sum of quantities of all drug degradation products present in the aerosol)/((quantity of drug(s) present in the aerosol)+(sum of quantities of all drug degradation products present in the aerosol)). The term "percent drug degradation product" as used herein refers to the fraction drug degradation product multiplied by 100%, whereas "purity" of the aerosol refers to 100% minus the percent drug degradation products.

"Heat stable drug" refers to a drug that has a TSR≥9 when vaporized from a film of some thickness between 0.05 µm and 20 µm.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Number concentration" refers to the number of particles per unit volume of aerosol.

"Purity" as used herein, with respect to the aerosol purity, means the fraction of drug composition in the aerosol/the fraction of drug composition in the aerosol plus drug degradation products. Thus purity is relative with regard to the purity of the starting material. For example, when the starting drug or drug composition used for substrate coating contained detectable impurities, the reported purity of the aerosol does not include those impurities present in the starting material that were also found in the aerosol, e.g., in certain cases if the starting material contained a 1% impurity and the aerosol was found to contain the identical 1% impurity, the aerosol purity may nevertheless be reported as >99% pure, reflecting the fact that the detectable 1% purity was not produced during the vaporization-condensation aerosol generation process.

"Settling velocity" refers to the terminal velocity of an aerosol particle undergoing gravitational settling in air.

"Support" refers to a material on which the composition is adhered, typically as a coating or thin film. The term "support" and "substrate" are used herein interchangeably.

"Substantially free of" means that the material, compound, aerosol, etc., being described is at least 95% free of the other component from which it is substantially free.

"Typical patient tidal volume" refers to 1 L for an adult patient and 15 mL/kg for a pediatric patient.

"Therapeutically effective amount" means the amount required to achieve a therapeutic effect. The therapeutic effect could be any therapeutic effect ranging from prevention, symptom amelioration, symptom treatment, to disease termination or cure.

"Thermal stability ratio" or "TSR" means the % purity/(100%-% purity) if the % purity is <99.9%, and 1000 if the % purity is ≥99.9%. For example, a respiratory drug vaporizing at 90% purity would have a TSR of 9.

"4 μm thermal stability ratio" or "4TSR" means the TSR of a drug determined by heating a drug-comprising film of about 4 microns in thickness under conditions sufficient to vaporize at least 50% of the drug in the film, collecting the resulting aerosol, determining the purity of the aerosol, and using the purity to compute the TSR. In such vaporization, generally the about 4-micron thick drug film is heated to around 350° C. but not less than 200° C. for around 1 second to vaporize at least 50% of the drug in the film.

"1.5 μm thermal stability ratio" or "1.5TSR" means the TSR of a drug determined by heating a drug-comprising film of about 1.5 microns in thickness under conditions sufficient to vaporize at least 50% of the drug in the film, collecting the resulting aerosol, determining the purity of the aerosol, and using the purity to compute the TSR. In such vaporization, generally the about 1.5-micron thick drug film is heated to around 350° C. but not less than 200° C. for around 1 second to vaporize at least 50% of the drug in the film.

"0.5 μm thermal stability ratio" or "0.5TSR" means the TSR of a drug determined by heating a drug-comprising film of about 0.5 microns in thickness under conditions sufficient to vaporize at least 50% of the drug in the film, collecting the resulting aerosol, determining the purity of the aerosol, and using the purity to compute the TSR. In such vaporization, generally the about 0.5-micron thick drug film is heated to around 350° C. but not less than 200° C. for around 1 second to vaporize at least 50% of the drug in the film.

"Vapor" refers to a gas, and "vapor phase" refers to a gas phase. The term "thermal vapor" refers to a vapor phase, aerosol, or mixture of aerosol-vapor phases, formed preferably by heating.

Nicotine is a heterocyclic compound that can exist in both a free base and salt forms. The free base form has the following structure:

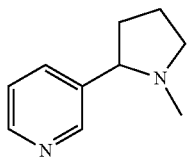

At 25° C., nicotine is a colorless to pale yellow volatile liquid. Nicotine has a melting point of −79° C., a boiling point at 247° C., and a vapor pressure of 0.0425 mmHg at 25° C. The liquid nature prevents formation of stable films and the high vapor pressure can result in evaporation during shelf-life storage. While various approaches for preventing nicotine evaporation and degradation during shelf-life storage have been considered, for example, delivery from a reservoir via ink jet devices, chemical encapsulation of nicotine as a cyclodextrin complex, and nicotine containment in blister packs, such implementations have not been demonstrated to be amendable to low-cost manufacturing, nor easy to reduce to practice in actual devices.

Nicotine Meta-Salicylate

Figure 2:
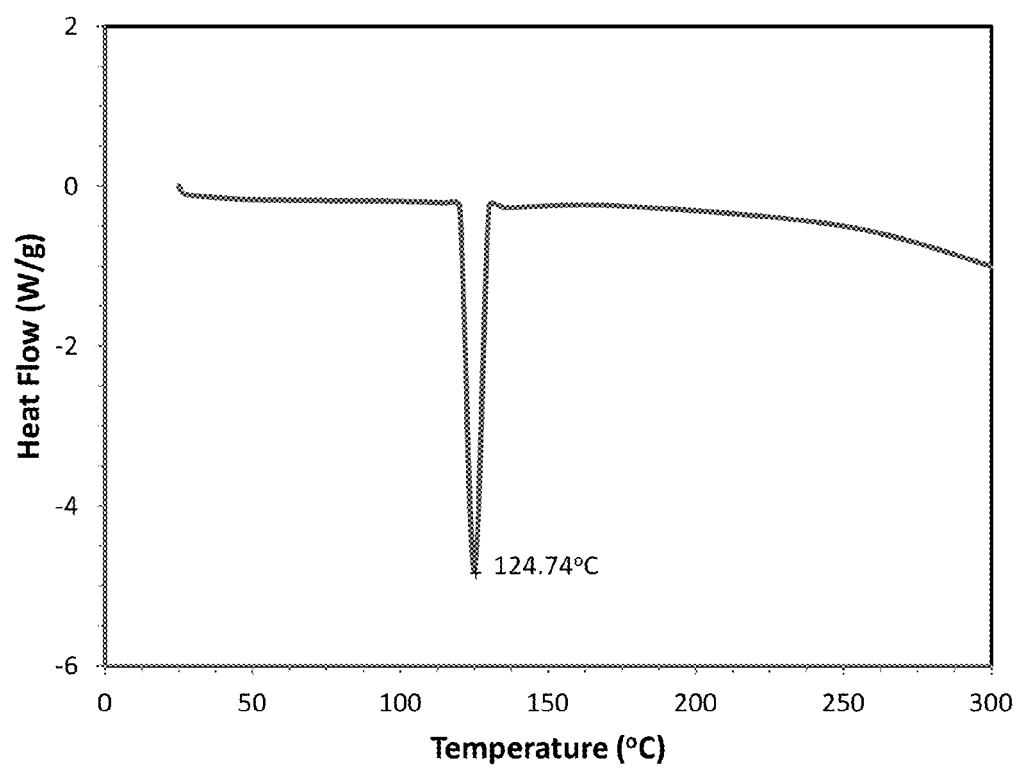
FIG. 2 shows a typical calorimetric scan of nicotine m-salicylate powder.
Figure 3:
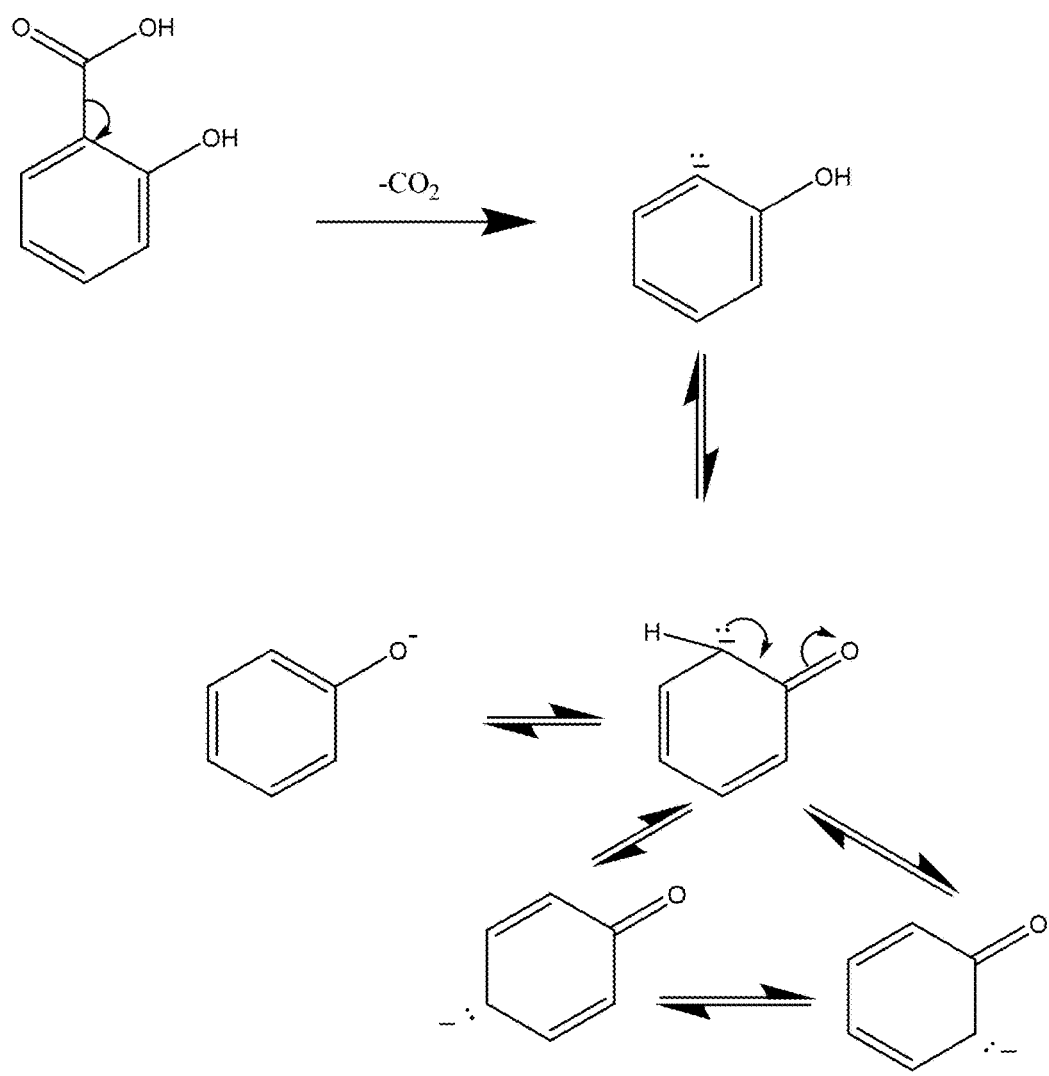
FIG. 3 shows the ortho isomer.
Figure 4:
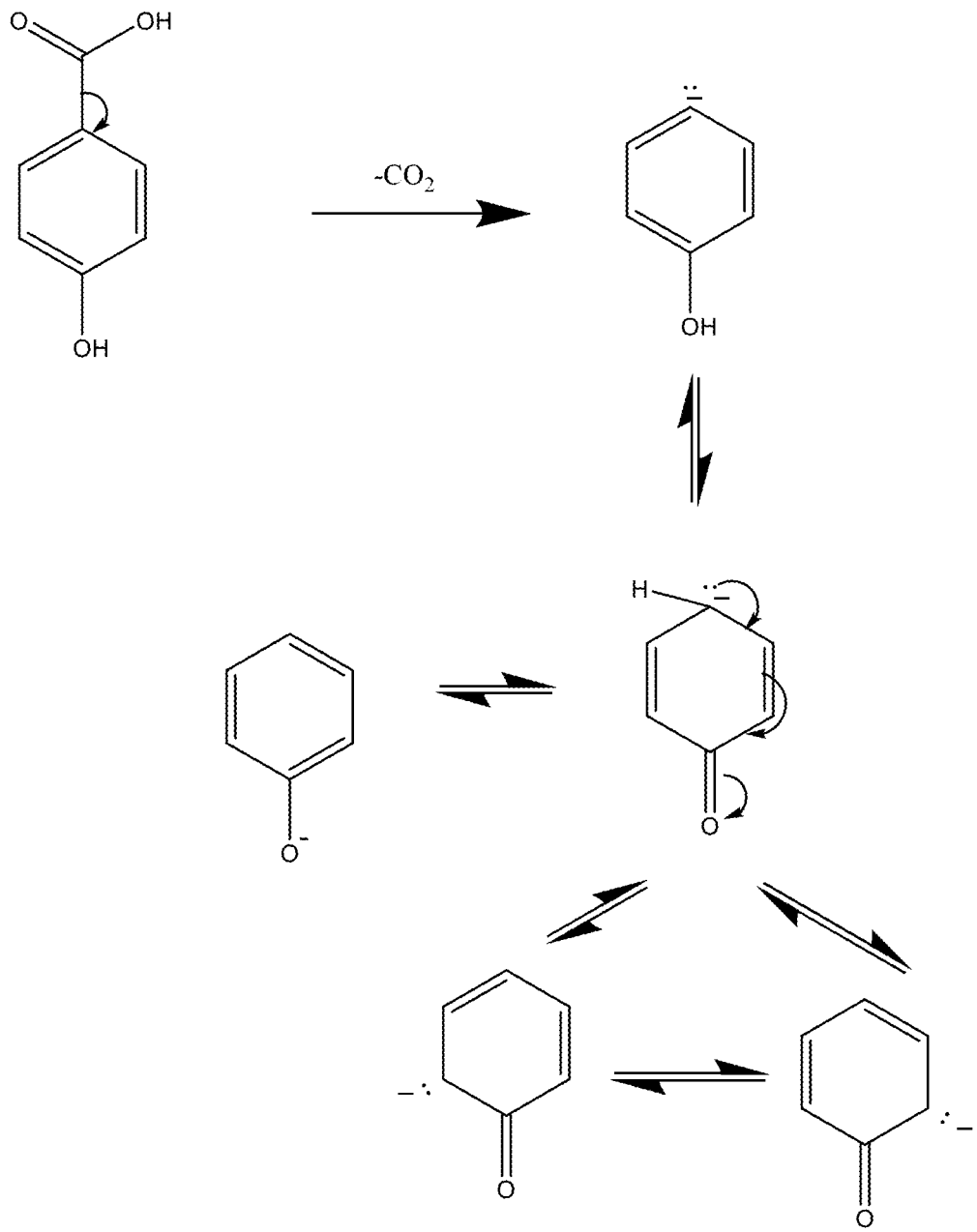
FIG. 4 shows the para isomer.
Figure 5:
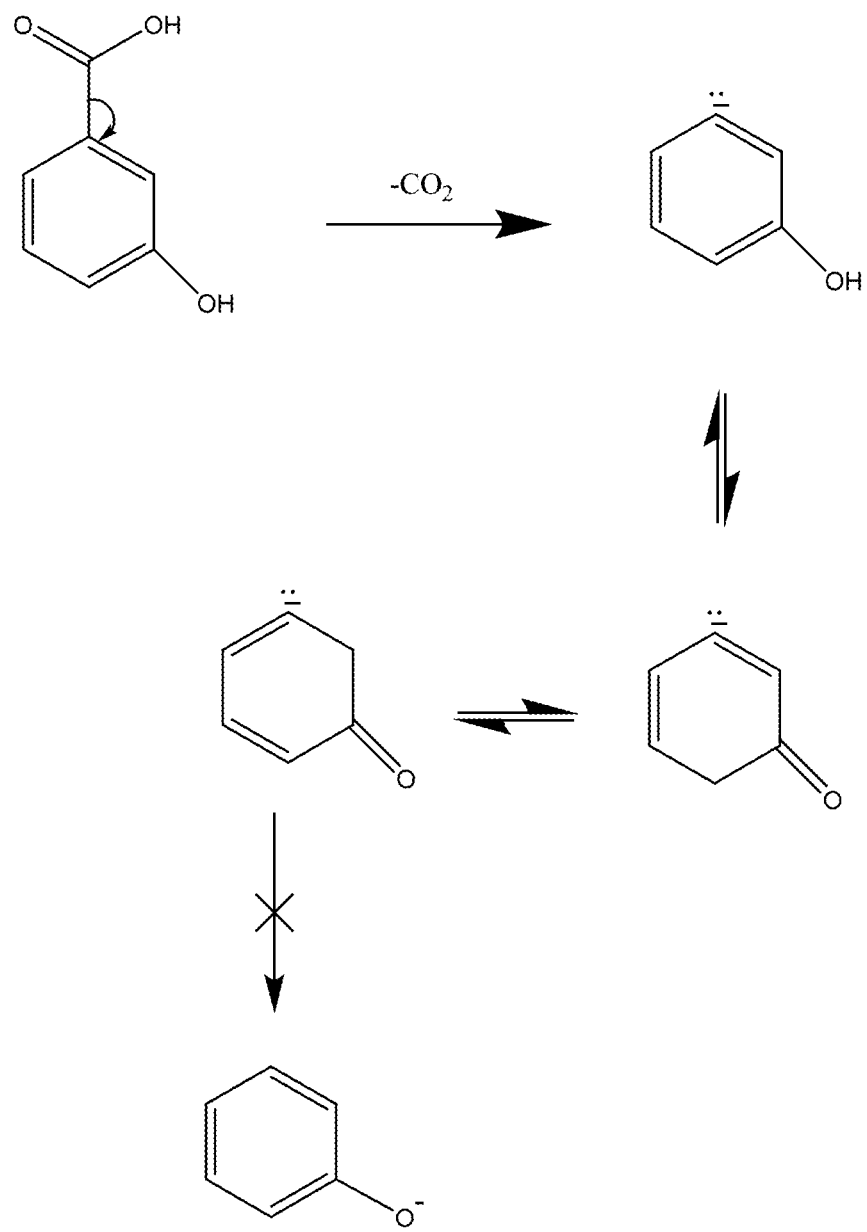
FIG. 5 shows the meta isomer.
Figure 6:
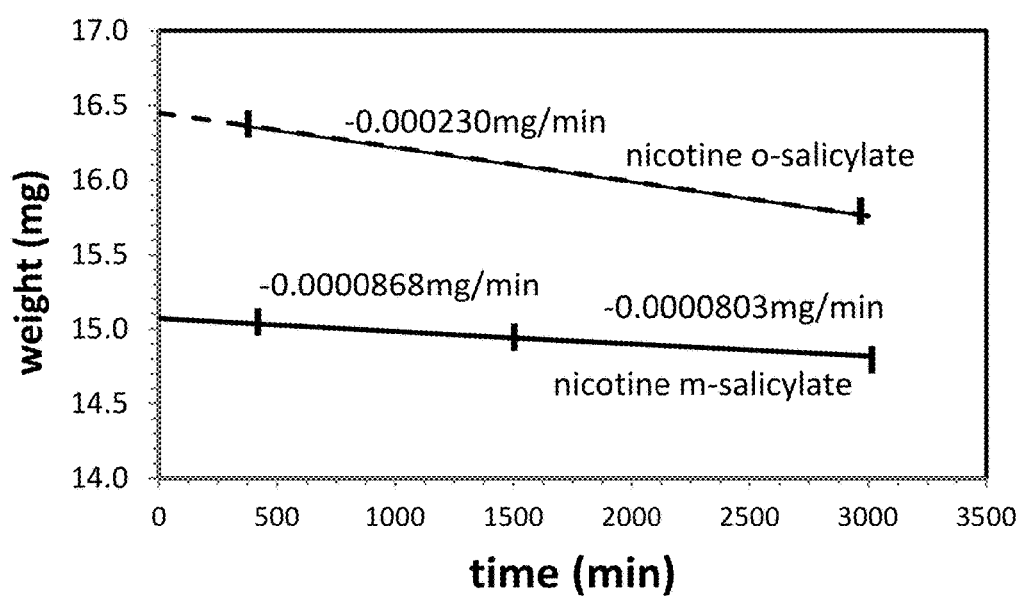
FIG. 6 is a thermogravimetric analysis plot showing the isothermal mass loss of the nicotine meta-salicylate is less than that of nicotine ortho-salicylate.

The structure of meta-salicylic acid, also known as 3-hydroxybenzoic acid, is shown in FIG. 2. This disclosure teaches a nicotine salt with the meta-salicylic acid. The synthesis of nicotine meta-salicylate is described in Example 1.

The nicotine meta-salicylate has two potentially important advantages over the commercially available nicotine ortho-salicylate. First, thermogravimetric analysis data show that isothermal mass loss of the nicotine meta-salicylate can be less than that of the nicotine ortho-salicylate. For example, at storage temperatures between 40-60° C., nicotine mass loss from nicotine meta-salicylate was about 2-3× less than nicotine ortho-salicylate.

Mass loss due to evaporation of the nicotine and/or salicylic acid is detrimental in view of the produces stability, i.e, the ability to provide consistent dosing of the drug over the shelf life of the product. The meta-salicylate salt is less prone to thermal degradation during vaporization, particularly with regards to formation of phenol. This is another distinct advantage of the present disclosure. The position of the hydroxyl group on the salicylic acid can affect the likelihood of the decarboxylation of salicylic acid into phenol by contributing (or not contributing) to resonance stabilization of an ion or free radical. The ortho (and para) isomers have resonance structures where the negative charge is localized on the oxygen atom, whereas this structure cannot form for the meta isomer. This structure increases the stability of the ion/radical and therefore increases the likelihood or rate of the phenol formation from ortho- or para-salicylic acid.

Aerosol Composition

The compositions described herein typically comprise nicotine compounds. The compositions may comprise other compounds as well. For example, the composition may comprise a mixture of drug compounds, a mixture of a nicotine compound and a pharmaceutically acceptable excipient, or a mixture of a nicotine compound with other compounds having useful or desirable properties. The composition may comprise a pure nicotine compound as well. In preferred embodiments, the composition consists essentially of pure nicotine meta-salicylate and contains no propellants or solvents.

Additionally, pharmaceutically acceptable carriers, surfactants, enhancers, and inorganic compounds may be included in the composition. Examples of such materials are known in the art.

In some variations, the aerosols are substantially free of organic solvents and propellants. Additionally, water is typically not added as a solvent for the nicotine meta-salicylate, although water from the atmosphere may be incorporated in the aerosol during formation, in particular, while passing air over the film and during the cooling process. In other variations, the aerosols are completely devoid of organic solvents and propellants. In yet other variations, the aerosols are completely devoid of organic solvents, propellants, and any excipients. These aerosols comprise only pure drug, less than 10% drug degradation products, and a carrier gas, which is typically air.

Typically, the drug has a decomposition index less than 0.15. Preferably, the drug has a decomposition index less than 0.10. More preferably, the drug has a decomposition index less than 0.05. Most preferably, the drug has a decomposition index less than 0.025

In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations, the condensation aerosol particles comprise less than 10% by weight of a thermal degradation product. In other variations, the condensation drug aerosol particles comprise less than 5%, 1%, 0.5%, 0.1%, or 0.03% by weight of a thermal degradation product.

In certain embodiments of the disclosure, the drug aerosol has a purity of between 90% and 99.8%, or between 93% and 99.7%, or between 95% and 99.5%, or between 96.5% and 99.2%. In certain embodiments of the disclosure, the drug aerosol has percent of freebase nicotine in the aerosol of between 90% and 99.8%, or between 93% and 99.7%, or between 95% and 99.5%, or between 96.5% and 99.2%.

Typically, the aerosol has a number concentration greater than $10^6$ particles/mL. In other variations, the aerosol has a number concentration greater than $10^7$ particles/mL. In yet other variations, the aerosol has a number concentration greater than $10^8$ particles/mL, greater than $10^9$ particles/mL, greater than $10^{10}$ particles/mL, or greater than $10^{11}$ particles/mL.

The gas of the aerosol typically is air. Other gases, however, can be used, in particular inert gases, such as argon, nitrogen, helium, and the like. The gas can also include vapor of the composition that has not yet condensed to form particles. Typically, the gas does not include propellants or vaporized organic solvents. In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations the condensation drug aerosol has a MMAD in the range of about 0.01-3 µm. In some variations the condensation drug aerosol has a MMAD in the range of about 0.1-3 µm. In some variations the geometric standard deviation around the MMAD of the condensation drug aerosol particles is less than 3.0. In other variations, the geometric standard deviation around the MMAD of the condensation drug aerosol particles is less than 2.5, or less than 2.0.

In certain embodiments of the invention, the drug aerosol comprises one or more drugs having a 4TSR of at least 5 or 10, a 1.5TSR of at least 7 or 14, or a 0.5TSR of at least 9 or 18. In other embodiments of the invention, the drug aerosol comprises one or more drugs having a 4TSR of between 5 and 100 or between 10 and 50, a 1.5TSR of between 7 and 200 or between 14 and 100, or a 0.5TSR of between 9 and 900 or between 18 and 300.

Formation of Condensation Aerosols

Any suitable method may be used to form the condensation aerosols described herein. One such method involves the heating of a composition to form a vapor, followed by cooling of the vapor so that it forms an aerosol (i.e., a condensation aerosol). Methods have been previously described in U.S. Pat. No. 7,090,830. This reference is hereby incorporated by reference in its entirety.

Typically, the composition is coated on a substrate, and then the substrate is heated to vaporize the composition. The substrate may be of any geometry and be of a variety of different sizes. It is often desirable that the substrate provide a large surface to volume ratio (e.g., greater than 100 per meter) and a large surface to mass ratio (e.g., greater than 1 $cm^2$ per gram). The substrate can have more than one surface A substrate of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials may be used to construct the substrate. Typically, the substrates are heat-conductive and include metals, such as aluminum, iron, copper, stainless steel, and the like, alloys, ceramics, and filled polymers. In one variation, the substrate is stainless steel. Combinations of materials and coated variants of materials may be used as well.

When it is desirable to use aluminum as a substrate, aluminum foil is a suitable material. Examples of alumina and silicon based materials BCR171 (an alumina of defined surface area greater than 2 $m^2$/g from Aldrich, St. Louis, Mo.) and a silicon wafer as used in the semiconductor industry.

Typically it is desirable that the substrate have relatively few, or substantially no, surface irregularities. Although a variety of supports may be used, supports that have an impermeable surface, or an impermeable surface coating, are typically desirable. Illustrative examples of such supports include metal foils, smooth metal surfaces, nonporous ceramics, and the like. Alternatively, or in addition, to preferred substrates having an impermeable surface, the substrate surface expanse is characterized by a contiguous surface area of about 20 $mm^2$. Alternatively, or in addition, to preferred substrates having an impermeable surface, the substrate surface expanse is characterized by a contiguous surface area of greater than 1 $mm^2$, preferably 10 $mm^2$, more preferable 50 $mm^2$ and still more preferably 100 $mm^2$, and a material density of greater than 0.5 g/cc. In contrast, non-preferred substrates typically have a substrate density of less than 0.5g/cc, such as, for example, yarn, felts and foam, or have a surface area of less than 1 $mm^2$/particle such as, for example small alumina particles, and other inorganic particles, as it is difficult on these types of surfaces to generate therapeutic quantities of a drug aerosol with less than 10% drug degradation via vaporization.

In one variation, the disclosure teaches a stainless steel foil substrate. A hollow, stainless steel tube may be used as the drug-film substrate. In other variations, aluminum foil is used as a substrate for testing drug.

The composition is typically coated on the solid support in the form of a film. The film may be coated on the solid support using any suitable method. The method suitable for coating is often dependent upon the physical properties of the compound and the desired film thickness. One exemplary method of coating a composition on a solid support is by preparing a solution of compound (alone or in combination with other desirable compounds) in a suitable solvent, applying the solution to the exterior surface of the solid support, and then removing the solvent (e.g., via evaporation, etc.) thereby leaving a film on the support surface.

Common solvents include methanol, dichloromethane, methyl ethyl ketone, diethyl ether, acetone, ethanol, isopropyl alcohol, 3:1 chloroform:methanol mixture, 1:1 dichloromethane: methyl ethyl ketone mixture, dimethylformamide, and deionized water. In some instances (e.g., when triamterene is used), it is desirable to use a solvent such as formic acid. Sonication may also be used as necessary to dissolve the compound.

The composition may also be coated on the solid support by dipping the support into a composition solution, or by spraying, brushing or otherwise applying the solution to the support. Alternatively, a melt of the drug can be prepared and applied to the support. For drugs that are liquids at room temperature, thickening agents can be mixed with the drug to permit application of a solid drug film.

The film can be of varying thickness depending on the compound and the maximum amount of thermal degradation desired. In one method, the heating of the composition involves heating a thin film of the composition having a thickness between about 0.1 μm-30 μm to form a vapor. In yet other variations, the composition has a film thickness between about 0.5 μm-21 μm. Most typically, the film thickness vaporized is between 0.5 μm-25 μm.

The support on which the film of the composition is coated can be heated by a variety of means to vaporize the composition. Exemplary methods of heating include the passage of current through an electrical resistance element, absorption of electromagnetic radiation (e.g., microwave or laser light) and exothermic chemical reactions (e.g., exothermic solvation, hydration of pyrophoric materials, and oxidation of combustible materials). Heating of the substrate by conductive heating is also suitable. One exemplary heating source is described in U.S. patent application for SELF-CONTAINED HEATING UNIT AND DRUG-SUPPLY UNIT EMPLOYING SAME, U.S. Ser. No. 60/472,697 filed May 21, 2003. The description of the exemplary heating source disclosed therein, is hereby incorporated by reference.

Heat sources typically supply heat to the substrate at a rate that achieves a substrate temperature of at least 200° C., preferably at least 250° C., or more preferably at least 300° C. or 350° C., and produces substantially complete volatilization of the drug composition from the substrate within a period of 2 seconds, preferably, within 1 second, or more preferably within 0.5 seconds. Suitable heat sources include resistive heating devices which are supplied current at a rate sufficient to achieve rapid heating, e.g., to a substrate temperature of at least 200° C., 250° C., 300° C., or 350° C. preferably within 50-500 ms, more preferably in the range of 50-200 ms. Heat sources or devices that contain a chemically reactive material which undergoes an exothermic reaction upon actuation, e.g., by a spark or heat element, such as flashbulb type heaters of the type described in several examples, and the heating source described in the above-cited U.S. patent application for SELF-CONTAINED HEATING UNIT AND DRUG-SUPPLY UNIT EMPLOYING SAME, are also suitable. In particular, heat sources that generate heat by exothermic reaction, where the chemical "load" of the source is consumed in a period of between 50-500 msec or less are generally suitable, assuming good thermal coupling between the heat source and substrate.

When heating the thin film of the composition, to avoid decomposition, it is desirable that the vaporized compound should transition rapidly from the heated surface or surrounding heated gas to a cooler environment. This may be accomplished not only by the rapid heating of the substrate, but also by the use of a flow of gas across the surface of the substrate. While a vaporized compound from a surface may transition through Brownian motion or diffusion, the temporal duration of this transition may be impacted by the extent of the region of elevated temperature at the surface, which is established by the velocity gradient of gases over the surface and the physical shape of surface. Typical gas-flow rates used to minimize such decomposition and to generate a desired particle size are in the range of 1-10 L/minute.

The aerosol particles for administration can typically be formed using any of the describe methods at a rate of greater than $10^8$ inhalable particles per second. In some variations, the aerosol particles for administration are formed at a rate of greater than $10^9$ or $10^{10}$ inhalable particles per second. Similarly, with respect to aerosol formation (i.e., the mass of aerosolized particulate matter produced by a delivery device per unit time) the aerosol may be formed at a rate greater than 0.25 mg/second, greater than 0.5 mg/second, or greater than 1 or 2 mg/second. Further, with respect to aerosol formation, focusing on the drug aerosol formation rate (i.e., the rate of drug compound released in aerosol form by a delivery device per unit time), the drug may be aerosolized at a rate greater than 0.05 mg drug per second, greater than 0.1 mg drug per second, greater than 0.5 mg drug per second, or greater than 1 or 2 mg drug per second.

In some variations, the drug condensation aerosols are formed from compositions that provide at least 5% by weight of drug condensation aerosol particles. In other variations, the aerosols are formed from compositions that provide at least 10%, 20%, 30%, 40%, 50%, 60%, or 75% by weight of drug condensation aerosol particles. In still other variations, the aerosols are formed from compositions that provide at least 95%, 99%, or 99.5% by weight of drug condensation aerosol particles.

In some variations, the drug condensation aerosol particles when formed comprise less than 10% by weight of a thermal degradation product. In other variations, the drug condensation aerosol particles when formed comprise less than 5%, 1%, 0.5%, 0.1%, or 0.03% by weight of a thermal degradation product.

In some variations the drug condensation aerosols are produced in a gas stream at a rate such that the resultant aerosols have a MMAD in the range of about 0.1-3 μm. In some variations the geometric standard deviation around the MMAD of the drug condensation aerosol particles is less than 3.0. In other variations, the geometric standard deviation around the MMAD of the drug condensation aerosol particles is less than 2.5, or less than 2.0.

Delivery Devices

The delivery devices described herein for administering a condensation drug aerosol typically comprise an element for heating the composition to form a vapor and an element allowing the vapor to cool, thereby forming a condensation aerosol. These aerosols are generally delivered via inhalation to lungs of a patient, for local or systemic treatment. Alternatively, however, the condensation aerosols of the invention can be produced in an air stream, for application of drug-aerosol particles to a target site. For example, a stream of air carrying drug-aerosol particles can be applied to treat an acute or chronic skin condition, can be applied during surgery at the incision site, or can be applied to an open wound. The delivery device may be combined with a composition comprising a drug in unit dose form for use as a kit.

The devices described herein may additionally contain a variety of components to facilitate aerosol delivery. For instance, the device may include any component known in the art to control the timing of drug aerosolization relative to inhalation (e.g., breath-actuation). Similarly, the device may include a component to provide feedback to patients on the rate and/or volume of inhalation, or a component to prevent excessive use (i.e. , "lockout" feature). The device may further comprise features such as dose counting/logging or tapering methods. In addition, the device may further include a component to prevent use by unauthorized individuals, and a component to record dosing histories. These components may be used alone, or in combination with other components. Additionally, the devices may contain features to allow for the tapering off of nicotine dose.

The element that allows cooling may be of any configuration. For example, it may be an inert passageway linking the heating means to the inhalation means. Similarly, the element permitting inhalation by a user may be of any configuration. For example, it may be an exit portal that forms a connection between the cooling element and the user's respiratory system.

Typically, the drug supply article is heated to a temperature sufficient to vaporize all or a portion of the film, so that the composition forms a vapor that becomes entrained in a stream of air during inhalation. As noted above, heating of the drug supply article may be accomplished using, for example, an electrically-resistive wire embedded or inserted into the substrate and connected to a battery disposed in the housing. The heating can be actuated, for example, with a button on the housing or via breath actuation, as is known in the art.

Another device that may be used to form and deliver the aerosols described herein is as follows. The device comprises an element for heating a composition to form a vapor, an element allowing the vapor to cool, thereby forming a condensation aerosol, and an element permitting a user to inhale the aerosol. The device also comprises an upper external housing member and a lower external housing member that fit together.

The downstream end of each housing member is gently tapered for insertion into a user's mouth. The upstream end of the upper and lower housing members are slotted (either one or both are slotted), to provide for air intake when a user inhales. The upper and lower housing members when fitted together define a chamber. Positioned within chamber is a drug supply unit.

The solid support may be of any desirable configuration. At least a portion of the surface of the substrate is coated with a composition film. With the case of the thermite-type heating source, the interior region of the substrate contains a substance suitable to generate heat. The substance can be a solid chemical fuel, chemical reagents that mix exothermically, electrically resistive wire, etc. A power supply source, if needed for heating, and any necessary valving for the inhalation device may be contained in end piece. A power supply source may be a piece that mates with the drug supply unit.

In one variation of the devices used, the device includes a drug composition delivery article composed of the substrate, a film of the selected drug composition on the substrate surface, and a heat source for supplying heat to the substrate at a rate effective to heat the substrate to a temperature greater than 200° C. or in other embodiments to a temperature greater than 250° C., 300° C. or 350° C., and to produce substantially complete volatilization of the drug composition within a period of 2 seconds or less.

Other drug supply articles that may be used in combination with the devices described herein. Various methods of coatings are known in the art and/or have been described above.

The illustrative heating element shown as an electrical resistive wire that produces heat when a current flows through it, but as noted above, a number of different heating methods and corresponding devices are acceptable. For example, acceptable heat sources can supply heat to the drug supply article at rates that rapidly achieve a temperature sufficient to completely vaporize the composition from the support surface. For example, heat sources that achieve a temperature of 200° C. to 500° C. or more within a period of 2 seconds are typical, although it should be appreciated that the temperature chosen will be dependent upon the vaporization properties of the composition, but is typically heated to a temperature of at least about 200° C., preferably of at least about 250° C., more preferably at least about 300° C. or 350° C. Heating the substrate produces a drug composition vapor that in the presence of the flowing gas generates aerosol particles in the desired size range. The presence of the gas flow is generally prior to, simultaneous with, or subsequent to heating the substrate. In one embodiment, the substrate is heated for a period of less than about 1 second, and more preferably for less than about 500 milliseconds, still more preferably for less than about 200 milliseconds. The drug-aerosol particles are inhaled by a subject for delivery to the lung.

The device may also include a gas-flow control valve disposed upstream of the solid support, for limiting gas-flow rate through the condensation region. The gas-flow valve may, for example, include an inlet port communicating with the chamber, and a deformable flap adapted to divert or restrict airflow away from the port increasingly, with increasing pressure drop across the valve. Similarly, the gas-flow valve may include an actuation switch. In this variation, the valve movement would be in response to an air pressure differential across the valve, which for example, could function to close the switch. The gas-flow valve may also include an orifice designed to limit airflow rate into the chamber.

The device may also include a bypass valve communicating with the chamber downstream of the unit for offsetting the decrease in airflow produced by the gas-flow control valve, as the user draws air into the chamber. In this way, the bypass valve could cooperate with the gas-control valve to control the flow through the condensation region of the chamber as well as the total amount of air being drawn through the device. Thus the total volumetric airflow through the device in this variation would be the sum of the volumetric airflow rate through the gas-control valve and the volumetric airflow rate through the bypass valve.

The gas control valve could, for example, function to limit air drawn into the device to a preselected level, e.g., 15 L/minute. In this way, airflow for producing particles of a desired size may be preselected and produced. For example, once this selected airflow level is reached, additional air drawn into the device would create a pressure drop across the bypass valve, which in turn would accommodate airflow through the bypass valve into the downstream end of the device adjacent the user's mouth. Thus, the user senses a full breath being drawn in, with the two valves distributing the total airflow between desired airflow rate and bypass airflow rate.

These valves may be used to control the gas velocity through the condensation region of the chamber and hence to control the particle size of the aerosol particles produced. Typically, the faster the airflow, the smaller the particles are. Thus, to achieve smaller or larger particles, the gas velocity through the condensation region of the chamber may be altered by modifying the gas-flow control valve to increase or decrease the volumetric airflow rate. For example, to produce condensation particles in the size range of about 1-3.5 pm MMAD, a chamber having substantially smooth-surfaced walls would have a selected gas-flow rate in the range of 1-10 L/minute.

Additionally, as will be appreciated by one of skill in the art, particle size may be altered by modifying the cross-section of the chamber condensation region to increase or decrease linear gas velocity for a given volumetric flow rate, and/or the presence or absence of structures that produce turbulence within the chamber. Thus, for example to produce condensation particles in the size range 10-100 nm MMAD, the chamber may provide gas-flow barriers for creating air turbulence within the condensation chamber.

These barriers are typically placed within a few thousandths of an inch from the substrate surface. Particle size is discussed in more detail below.

Drug Composition Film Thickness

Typically, the drug composition film coated on the solid support has a thickness of between about 0.05-30 µm, and typically a thickness between 0.1-30 µm. More typically, the thickness is between about 0.2-30 µm; even more typically, the thickness is between about 0.5-30 µm, and most typically, the thickness is between about 0.5-25 µm. The desirable film thickness for any given drug composition is typically determined by an iterative process in which the desired yield and purity of the condensation aerosol composition are selected or known.

For example, if the purity of the particles is less than that which is desired, or if the percent yield is less than that which is desired, the thickness of the drug film is adjusted to a thickness different from the initial film thickness. The purity and yield are then determined at the adjusted film thickness, and this process is repeated until the desired purity and yield are achieved. After selection of an appropriate film thickness, the area of substrate required to provide a therapeutically effective dose is determined.

Generally, the film thickness for a given drug composition is such that drug-aerosol particles, formed by vaporizing the drug composition by heating the substrate and entraining the vapor in a gas stream, have (i) 10% by weight or less drug-degradation product, more preferably 5% by weight or less, most preferably 2.5% by weight or less and (ii) at least 50% of the total amount of drug composition contained in the film. The area of the substrate on which the drug composition film is formed is selected to achieve an effective human therapeutic dose of the drug aerosol as is described further below.

To determine the thickness of the drug film, one method that can be used is to determine the area of the substrate and calculate drug film thickness using the following relationship:

film thickness (cm)=drug mass (g)/[drug density (g/cm$^3$)×substrate area (cm$^2$)]

The drug mass can be determined by weighing the substrate before and after formation of the drug film or by extracting the drug and measuring the amount analytically. Drug density can be experimentally determined by a variety of techniques, known by those of skill in the art or found in the literature or in reference texts, such as in the CRC. An assumption of unit density is acceptable if an actual drug density is not known.

The substrate having a drug film of known thickness was heated to a temperature sufficient to generate a thermal vapor. All or a portion of the thermal vapor was recovered and analyzed for presence of drug-degradation products, to determine purity of the aerosol particles in the thermal vapor. There is a clear relationship between film thickness and aerosol particle purity, whereas the film thickness decreases, the purity increases.

In addition to selection of a drug film thickness that provides aerosol particles containing 10% or less drug-degradation product (i.e., an aerosol particle purity of 90% or more), the film thickness is selected such that at least about 50% of the total amount of drug composition contained in the film is vaporized when the substrate is heated to a temperature sufficient to vaporize the film.

To obtain higher purity aerosols one can coat a lesser amount of drug, yielding a thinner film to heat, or alternatively use the same amount of drug but a larger surface area.

Generally, except for, as discussed above, extremely thin thickness of drug film, a linear decrease in film thickness is associated with a linear decrease in impurities.

Thus for the drug composition where the aerosol exhibits an increasing level of drug degradation products with increasing film thicknesses, particularly at a thickness of greater than 0.05-30 microns, the film thickness on the substrate will typically be between 0.05 and 30 microns, e.g., the maximum or near-maximum thickness within this range that allows formation of a particle aerosol with drug degradation less than 5%.

Another approach contemplates generation of drug-aerosol particles having a desired level of drug composition purity by forming the thermal vapor under a controlled atmosphere of an inert gas, such as argon, nitrogen, helium, and the like.

Once a desired purity and yield have been achieved or can be estimated from a graph of aerosol purity versus film thickness and the corresponding film thickness determined, the area of substrate required to provide a therapeutically effective dose is determined.

Substrate Area

As noted above, the surface area of the substrate surface area is selected such that it is sufficient to yield a therapeutically effective dose. The amount of drug to provide a therapeutic dose is generally known in the art and is discussed more below. The required dosage and selected film thickness, discussed above, dictate the minimum required substrate area in accord with the following relationship:

film thickness (cm)×drug density (g/cm$^3$)×substrate area (cm$^2$)=dose (g)

OR

Substrate area (cm$^2$)=dose (g)/[film thickness (cm)× drug density (g/cm$^3$)]

The drug mass can be determined by weighing the substrate before and after formation of the drug film or by extracting the drug and measuring the amount analytically. Drug density can be determined experimentally by a variety of well-known techniques, or may be found in the literature or in reference texts, such as in the CRC. An assumption of unit density is acceptable if an actual drug density is not known.

To prepare a drug supply article comprised of a drug film on a heat-conductive substrate that is capable of administering an effective human therapeutic dose, the minimum substrate surface area is determined using the relationships described above to determine a substrate area for a selected film thickness that will yield a therapeutic dose of drug aerosol.

In some variations, the selected substrate surface area is between about 0.05-500 cm$^2$. In others, the surface area is between about 0.05 and 300 cm$^2$. In one embodiment, the substrate surface area is between 0.05 and 0.5 cm$^2$. In one embodiment, substrate surface areas, are between 0.1 and 0.2 cm$^2$ The actual dose of drug delivered, i.e., the percent yield or percent emitted, from the drug-supply article will depend on, along with other factors, the percent of drug film that is vaporized upon heating the substrate. Thus, for drug films that yield upon heating 100% of the drug film and aerosol particles that have a 100% drug purity, the relationship between dose, thickness, and area given above correlates directly to the dose provided to the user. As the percent yield and/or particle purity decrease, adjustments in the substrate area can be made as needed to provide the desired dose. Also, as one of skill in the art will recognize, larger substrate areas other than the minimum calculated area for a particular film thickness can be used to deliver a therapeutically effective dose of the drug. Moreover as can be appreciated by one of skill in art, the film need not coat the complete surface area if a selected surface area exceeds the minimum required for delivering a therapeutic dose from a selected film thickness.

Dosage of Drug Containing Aerosols

The dose of a drug delivered in the aerosol refers to a unit dose amount that is generated by heating of the drug under defined conditions, cooling the ensuing vapor, and delivering the resultant aerosol. A "unit dose amount" is the total amount of drug in a given volume of inhaled aerosol. The unit dose amount may be determined by collecting the aerosol and analyzing its composition as described herein, and comparing the results of analysis of the aerosol to those of a series of reference standards containing known amounts of the drug. The amount of drug or drugs required in the starting composition for delivery as an aerosol depends on the amount of drug or drugs entering the thermal vapor phase when heated (i.e., the dose produced by the starting drug or drugs), the bioavailability of the aerosol drug or drugs, the volume of patient inhalation, and the potency of the aerosol drug or drugs as a function of plasma drug concentration.

One can determine the appropriate dose of a drug-containing aerosol to treat a particular condition using methods such as animal experiments and a dose-finding (Phase I/II) clinical trial. These experiments may also be used to evaluate possible pulmonary toxicity of the aerosol. One animal experiment involves measuring plasma concentrations of drug in an animal after its exposure to the aerosol. Mammals such as dogs or primates are typically used in such studies, since their respiratory systems are similar to that of a human and they typically provide accurate extrapolation of test results to humans. Initial dose levels for testing in humans are generally less than or equal to the dose in the mammal model that resulted in plasma drug levels associated with a therapeutic effect in humans Dose escalation in humans is then performed, until either an optimal therapeutic response is obtained or a dose-limiting toxicity is encountered. The actual effective amount of drug for a particular patient can vary according to the specific drug or combination thereof being utilized, the particular composition formulated, the mode of administration and the age, weight, and condition of the patient and severity of the episode being treated.

Particle Size

Efficient aerosol delivery to the lungs requires that the particles have certain penetration and settling or diffusional characteristics. Deposition in the deep lungs occurs by gravitational settling and requires particles to have an effective settling size, defined as mass median aerodynamic diameter (MMAD), typically between 1-3.5 μm. For smaller particles, deposition to the deep lung occurs by a diffusional process that requires having a particle size in the 10-100 nm, typically 20-100 nm range. An inhalation drug-delivery device for deep lung delivery should produce an aerosol having particles in one of these two size ranges, preferably between about 0.1-3 μm MMAD. Typically, in order to produce particles having a desired MMAD, gas or air is passed over the solid support at a certain flow rate.

During the condensation stage the MMAD of the aerosol is increasing over time. Typically, in variations of the invention, the MMAD increases within the size range of 0.01-3 microns as the vapor condenses as it cools by contact with the carrier gas then further increases as the aerosol particles collide with each other and coagulate into larger particles. Most typically, the MMAD grows from <0.5 micron to >1 micron in less than 1 second. Thus typically, immediately after condensing into particles, the condensation aerosol MMAD doubles at least once per second, often at least 2, 4, 8, or 20 times per second. In other variations, the MMAD increases within the size range of 0.1-3 microns.

Typically, the higher the flow rate, the smaller the particles that are formed. Therefore, in order to achieve smaller or larger particles, the flow rate through the condensation region of the delivery device may be altered. A desired particle size is achieved by mixing a compound in its vapor-state into a volume of a carrier gas, in a ratio such that the desired particle size is achieved when the number concentration of the mixture reaches approximately $10^9$ particles/mL. The particle growth at this number concentration is then slow enough to consider the particle size to be "stable" in the context of a single deep inhalation. This may be done, for example, by modifying a gas-flow control valve to increase or decrease the volumetric airflow rate. To illustrate, condensation particles in the size range 0.1-3 μm MMAD may be produced by selecting the gas-flow rate over the vaporizing drug to be in a range of 1-10 L/minute, preferably in the range of 2-8 L/min Additionally, as will be appreciated by one of skill in the art, particle size may also be altered by modifying the cross-section of the chamber condensation region to increase or decrease linear gas velocity for a given volumetric flow rate. In addition, particle size may also be altered by the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousandths of an inch from the substrate surface.

Analysis of Drug Containing Aerosols

Purity of a drug-containing aerosol may be determined using a number of different methods. It should be noted that when the term "purity" is used, it refers to the percentage of aerosol minus the percent byproduct produced in its formation. Byproducts for example, are those unwanted products produced during vaporization. For example, byproducts include thermal degradation products as well as any unwanted metabolites of the active compound or compounds. Examples of suitable methods for determining aerosol purity are described in Sekine et al., *Journal of Forensic Science* 32:1271-1280 (1987) and in Martin et al., *Journal of Analytic Toxicology* 13:158-162 (1989).

One suitable method involves the use of a trap. In this method, the aerosol is collected in a trap in order to determine the percent or fraction of byproduct. Any suitable trap may be used. Suitable traps include filters, glass wool, impingers, solvent traps, cold traps, and the like. Filters are often most desirable. The trap is then typically extracted with a solvent, e.g. acetonitrile, and the extract subjected to analysis by any of a variety of analytical methods known in the art, for example, gas, liquid, and high performance liquid chromatography particularly useful.

The gas or liquid chromatography method typically includes a detector system, such as a mass spectrometry detector or an ultraviolet absorption detector. Ideally, the detector system allows determination of the quantity of the components of the drug composition and of the byproduct, by weight. This is achieved in practice by measuring the signal obtained upon analysis of one or more known mass(es) of components of the drug composition or byproduct (standards) and then comparing the signal obtained upon analysis of the aerosol to that obtained upon analysis of the standard(s), an approach well known in the art.

In many cases, the structure of a byproduct may not be known or a standard for it may not be available. In such cases, one may calculate the weight fraction of the byproduct by assuming it has an identical response coefficient (e.g. for ultraviolet absorption detection, identical extinction coefficient) to the drug component or components in the drug composition. When conducting such analysis, byproducts present in less than a very small fraction of the drug compound, e.g. less than 0.1% or 0.03% of the drug compound, are typically excluded. Because of the frequent necessity to assume an identical response coefficient between drug and byproduct in calculating a weight percentage of byproduct, it is often more desirable to use an analytical approach in which such an assumption has a high probability of validity. In this respect, high performance liquid chromatography with detection by absorption of ultraviolet light at 225 nm is typically desirable. UV absorption at 250 nm may be used for detection of compounds in cases where the compound absorbs more strongly at 250 nm or for other reasons one skilled in the art would consider detection at 250 nm the most appropriate means of estimating purity by weight using HPLC analysis. In certain cases where analysis of the drug by UV are not viable, other analytical tools such as GC/MS or LC/MS may be used to determine purity.

It is possible that changing the gas under which vaporization of the composition occurs may also impact the purity.

Other Analytical Methods

Particle size distribution of a drug-containing aerosol may be determined using any suitable method in the art (e.g., cascade impaction). A Next Generation Cascade Impactor (MSP Corporation, Shoreview, Minn.) linked to a vaporization device by an induction port (USP induction port, MSP Corporation, Shoreview, Minn.) is one system used for cascade impaction studies.

Inhalable aerosol mass density may be determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the inhalation volume of an inhaling patient, typically about 2-4 liters.

Inhalable aerosol drug mass density may be determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the inhalation volume of an inhaling patient, typically about 2-4 liters. The amount of active drug compound collected in the chamber is determined by extracting the chamber, conducting chromatographic analysis of the extract and comparing the results of the chromatographic analysis to those of a standard containing known amounts of drug.

Inhalable aerosol particle concentration may be determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi * D^3 * \varphi / 6$, where D is a typical particle diameter in the size range (generally, the mean boundary MMADs defining the size range) in microns, φ is the particle density (in g/mL) and mass is given in units of picograms ($g^{-12}$).

Rate of inhalable aerosol particle formation may be determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 10 nm to 5 micron particles collected divided by the duration of the collection time.

Rate of aerosol formation may be determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation may be determined, for example, by delivering a drug-containing aerosol into a confined chamber via an inhalation device over a set period of time (e.g., 3 s). Where the aerosol is a pure drug, the amount of drug collected in the chamber is measured as described above. The rate of drug aerosol formation is equal to the amount of drug collected in the chamber divided by the duration of the collection time. Where the drug-containing aerosol comprises a pharmaceutically acceptable excipient, multiplying the rate of aerosol formation by the percentage of drug in the aerosol provides the rate of drug aerosol formation.

Kits

In an embodiment of the invention, a kit is provided for use by a healthcare provider, or more preferably a patient. The kit for delivering a condensation aerosol typically comprises a composition comprising a drug, and a device for forming a condensation aerosol. The composition is typically void of solvents and excipients and generally comprises a heat stable drug. The device for forming a condensation aerosol typically comprises an element configured to heat the composition to form a vapor, an element allowing the vapor to condense to form a condensation aerosol, and an element permitting a user to inhale the condensation aerosol. The device in the kit may further comprise features such as breath-actuation or lockout elements or dose counting/logging or tapering devices. An exemplary kit will provide a hand-held aerosol delivery device and at least one dose.

In another embodiment, kits for delivering a nicotine aerosol comprising a thin film of nicotine meta-salicylate composition and a device for dispensing said film as a condensation aerosol are provided. The composition may contain pharmaceutical excipients. The device for dispensing said film of a drug composition as an aerosol comprises an element configured to heat the film to form a vapor, and an element allowing the vapor to condense to form a condensation aerosol.

In the kits of the invention, the composition is typically coated as a thin film, generally at a thickness between about 0.5-30 microns, on a substrate which is heated by a heat source. Heat sources typically supply heat to the substrate at a rate that achieves a substrate temperature of at least 200° C., preferably at least 250° C., or more preferably at least 300° C. or 350° C., and produces substantially complete volatilization of the drug composition from the substrate within a period of 2 seconds, preferably, within 1 second, or more preferably within 0.5 seconds. To prevent drug degradation, it is preferable that the heat source does not heat the substrate to temperature greater than 600° C. while the drug film is on the substrate to prevent. More preferably, the heat source does not heat the substrate in to temperatures in excess of 500° C.

The kit of the invention can be comprised of various combinations of nicotine and drug delivery devices. In some embodiments the device may also be present with another drug. The other drug may be administered orally or topically. Generally, instructions for use are included in the kits.

In certain embodiments, thin films of nicotine meta-salicylate can be used to provide multiple doses of nicotine provided on a spool or reel of tape. For example, a tape can comprise a plurality of drug supply units with each drug supply unit comprising a heat package on which a thin film comprising nicotine meta-salicylate is disposed. Each heat package can include an initiator composition that can be ignited, for example, by resistive heating or percussively, and a fuel capable of providing a rapid, high temperature heat impulse sufficient to selectively vaporize the nicotine meta-salicylate. Each heat package can be spaced at intervals along the length of the tape. During use, one or more heat packages can be positioned within an airway and, while air is flowing through the airway, the heat package can be activated to selectively vaporize nicotine meta-salicylate. The vaporized nicotine can condense in the air flow to form an aerosol comprising the nicotine which can then be inhaled by a user. The tape can comprise a plurality of thin films that define the regions where the initiator composition, fuel, and thin film comprising nicotine meta-salicylate are disposed. Certain of the multiple layers can further provide unfilled volume for released gases to accumulate to minimize pressure buildup. The plurality of layers can be formed from any material which can provide mechanical support and that will not appreciably chemically degrade at the temperatures reached by the heat package. In certain embodiments, a layer can comprise a metal or a polymer such as polyimide, fluoropolymer, polyetherimide, polyether ketone, polyether sulfone, polycarbonate, or other high temperature resistance polymers. In certain embodiments, the tape can further comprise an upper and lower layer configured to physically and/or environmentally protect the drug. The upper and/or lower protective layers can comprise, for example, a metal foil, a polymer, or can comprise a multilayer comprising metal foil and polymers. In certain embodiments, protective layers can exhibit low permeability to oxygen, moisture, and/or corrosive gases. All or portions of a protective layer can be removed prior to use to expose a drug and fuel. The initiator composition and fuel composition can comprise, for example, any of those disclosed herein. Thin film heat packages and drug supply units in the form of a tape, disk, or other substantially planar structure, can provide a compact and manufacturable method for providing a large number of doses of a substance. Providing a large number of doses at low cost can be particularly useful in certain therapies, such as for example, in administering nicotine for the treatment of nicotine craving and/or effecting cessation of smoking.

The disclosure provides techniques for implementing drug delivery and drug cessation control. A drug delivery system might be provided having a form factor similar to a cigarette or cigar in the case that the drug is nicotine, nicotine meta-salicylate, or other nicotine related drug. Within the cigarette or cigar -shaped drug delivery device, a coil arrangement, a foil arrangement, or a resistive contact arrangement might form a circuit path to a current source. Each coil, foil, or resistive contact might be coated with the nicotine-based drug, or might be in thermal contact with a substrate coated with the nicotine-based drug. A control device might interface wirelessly with the cigarette or cigar -shaped drug delivery device to wirelessly control or manage delivery of the nicotine-based drug and to control cessation in the use of the drug In certain embodiments, the disclosure teaches a drug delivery and drug cessation system, comprising: a portable control device comprising a user input device, a first wireless transceiver, a second wireless transceiver, a processor, a memory device, and a network interface device; a drug delivery device comprising a third wireless transceiver, a dosage control device, a drug payload, and a dosage delivery device; and one or more user sensors each in contact with a portion of a body of a user, each of the one or more user sensors comprising a fourth wireless transceiver and one or more measurement sensors, the one or more measurement sensors comprising one or more of an oximeter, a pulse measurement sensor, a respiration rate sensor, or a blood pressure sensor. The user input device receives user inputs from the user to control drug delivery to the body of the user and to control drug cessation; the drug payload comprises a reservoir configured to contain amounts of a drug sufficient for one or more doses; the processor communicates with the drug delivery device via the first and third wireless transceivers to send first instructions to the dosage control device based on one or more of the user inputs, one or more preset instructions associated with drug delivery and drug cessation, or one or more measurement results from the one or more measurement sensors that are transmitted to the portable control device via the second and fourth wireless transceivers; the dosage control device determines an amount of the drug to be prepared for each dose based on the first instructions from the processor, and sends second instructions to the dosage delivery device to prepare and deliver the determined amount of the drug for delivery for each dose; the dosage delivery device delivers the drug from the drug payload to the user based on the second instructions from the dosage control device; the memory device stores a history of drug delivery using the system, the history of drug delivery comprising one or more of the one or more measurement results prior to each dose, drug dosages for each predetermined period, increases in drug dosage, decreases in drug dosage, number of doses for each predetermined period, increases in number of doses for each predetermined period, decreases in number of doses for each predetermined period, number of user-initiated drug delivery overrides, types of user-initiated drug delivery overrides, or contact information of a physician associated with the user; and the network interface communicatively couples with a computing device of the physician over a network to send the history of drug delivery to the physician and to receive drug dosage prescriptions from the physician.

The disclosure further teaches a drug delivery and drug cessation system, comprising: a portable drug delivery device comprising a drug payload, a dosage delivery device, and a first wireless transceiver; a portable control device comprising a second wireless transceiver, the portable control device being in wireless communication with the portable drug delivery device via the first wireless transceiver and the second wireless transceiver; the portable drug delivery device being configured to deliver a drug to a body of a user based on instructions received from the portable control device. The drug delivery device can be further characterized wherein the portable drug delivery device is a vapor-based drug delivery device.

The disclosure further teaches a drug delivery and drug cessation system, wherein the portable drug delivery device further comprises a breath actuator and a lockout unit, wherein the breath actuator is configured to cause the dosage delivery device to deliver a supplemental dose of the drug from the drug payload, based on a determination that the user has inhaled from the portable drug delivery device, and wherein the lockout unit is configured to prevent the breath actuator from causing the dosage delivery device to deliver the supplemental dose of the drug during a predetermined period based on a determination that the supplemental dose would exceed a predetermined maximum dose of the drug for the predetermined period.

The drug delivery and drug cessation system may be further characterized, wherein the breath actuator is configured to cause the dosage delivery device to deliver the supplemental dose of the drug from the drug payload, based on a determination that the user has inhaled from the portable drug delivery device, without receiving the instructions from the portable control device and contrary to any preset dosage schedule.

The drug delivery and drug cessation system may be further characterized, wherein the drug payload comprises one or more foils coated with the drug, wherein the dosage delivery device comprises a heater configured to heat one of a portion of each foil or an entire surface of each foil to at least 200 degrees Celsius within less than 2 seconds.

The drug delivery and drug cessation system may be further characterized wherein the heater is configured to heat one of a portion of each foil or an entire surface of each foil to at least 300 degrees Celsius within less than 0.5 seconds.

The drug delivery and drug cessation system may be further characterized, wherein the drug payload comprises a plurality of resistive coils connected in series and a plurality of fuses connected to a ground wire, each fuse separating each coil from a next adjacent coil in the series, wherein each of the plurality of coils is coated with the drug, wherein the dosage delivery device comprises a current source configured to heat each coil to at least 200 degrees Celsius within less than 2 seconds, wherein a circuit path is established from the current source to the plurality of coils in the series to the ground wire, with each fuse defining a short-circuit path between each coil and the next adjacent coil in the series, and wherein the current source is further configured to send a short current burst to cause an unfailed fuse closest to the current source to fail, thereby allowing the next adjacent coil in the series to be energized by the current source.

The drug delivery and drug cessation system may be further characterized, wherein the drug payload comprises a thin film structure comprising a plurality of foils connected in series and a plurality of fuses connected to a ground portion of the thin film structure, each fuse separating each foil from a next adjacent foil in the series, wherein each of the plurality of foils is coated with the drug, wherein the dosage delivery device comprises a current source configured to heat each foil to at least 200 degrees Celsius within less than 2 seconds, wherein a circuit path is established from the current source to the plurality of foils in the series to the ground wire, with each fuse defining a short-circuit path between each foil and the next adjacent foil in the series, and wherein the current source is further configured to send a short current burst to cause an unfailed fuse closest to the current source to fail, thereby allowing the next adjacent foil in the series to be energized by the current source.

The drug delivery and drug cessation system may be further characterized, wherein the thin film structure has an overall shape of one of a flat foil wrapped in wedge form, a flat foil wrapped in tubular form, or a planar structure.

The drug delivery and drug cessation system may be further characterized, wherein the portable drug delivery device is a transdermal-based drug delivery device.

The drug delivery and drug cessation system may be further characterized, wherein the drug payload comprises a liquid reservoir containing the drug in liquid form, wherein the dosage delivery device comprises a variable permeability membrane and a membrane actuator, said variable permeability membrane configured to change liquid permeability so as to deliver varying amounts of the drug from the liquid reservoir, based on control signals from the membrane actuator.

The drug delivery and drug cessation system may be further characterized, wherein the drug payload comprises a plurality of foils arranged in a first grid comprising a first plurality of rows and a first plurality of columns, each foil being coated with the drug and each foil being separated from each other by electrically and thermally non-conductive material, wherein the dosage delivery device comprises a first group of switches, a second group of switches, a current source electrically coupled to each of the first group of switches, an electrical ground path electrically coupled to each of the second group of switches, a plurality of actuators arranged in a second grid comprising a second plurality of rows and a second plurality of columns, a first plurality of linear electrical paths, a second plurality of linear electrical paths, wherein for each column in the second plurality of columns, a first electrical path is established from one of the first group of switches to each of the plurality of actuators arranged in the subject column in the second plurality of columns, wherein for each row in the second plurality of rows, a second electrical path is established from one of the second group of switches to each of the plurality of actuators arranged in the subject column in the second plurality of rows, wherein the plurality of foils arranged in the first grid is aligned with the plurality of actuators arranged in the second grid so as to make direct contact therewith.

The drug delivery and drug cessation system may be further characterized, wherein each of the plurality of actuators includes a resistive element configured to reach a temperature of at least 200 degrees Celsius within less than 2 seconds with application of a predetermined amount of current, wherein each of the plurality of foils arranged in the first grid is individually heated by closing one of the first group of switches and closing one of the second group of switches, thereby energizing a subject resistive element electrically coupled to both the one of the first group of switches and the one of the second group of switches, in turn heating a subject foil of the plurality of foils that is in direct contact with the subject resistive element.

The drug delivery and drug cessation system of may be further characterized, wherein the dosage delivery device further comprises a membrane in physical contact with the body of the user, wherein the drug heated by the subject foil flows as one of a gas or a liquid through the membrane to be absorbed by a skin portion of the body of the user.

The drug delivery and drug cessation system may be further characterized, wherein each switch in the first and second group of switches is a transistor.

The disclosure teaches a drug delivery and drug cessation system further comprising: one or more user sensors each in contact with a portion of the body of the user, each of the one or more user sensors comprising a third wireless transceiver and one or more measurement sensors, the one or more measurement sensors comprising one or more of an oximeter, a pulse measurement sensor, a respiration rate sensor, or a blood pressure sensor, wherein the portable drug delivery device is configured to deliver the drug to the body of the user based on instructions received from the portable control device and based on measurement results received from the one or more measurement sensors via the third wireless transceiver.

The disclosure teaches a drug delivery and drug cessation system, wherein the portable control device further comprises a memory device and a network interface, wherein the memory device is configured to store a history of drug delivery using the system, the history of drug delivery comprising one or more of drug dosages for each predetermined period, increases in drug dosage, decreases in drug dosage, number of doses for each predetermined period, increases in number of doses for each predetermined period, decreases in number of doses for each predetermined period, number of user-initiated drug delivery overrides, types of user-initiated drug delivery overrides, or contact information of a healthcare professional associated with the user, wherein the network interface communicatively couples with a computing device of the healthcare professional over a network to send the history of drug delivery to the healthcare professional and to receive drug dosage prescriptions from the healthcare professional.

The disclosure teaches a drug delivery and drug cessation method, comprising: providing a drug delivery and drug cessation system, comprising: a portable drug delivery device comprising a drug payload, a dosage delivery device, and a first wireless transceiver; and a portable control device comprising a second wireless transceiver, the portable control device being in wireless communication with the portable drug delivery device via the first wireless transceiver and the second wireless transceiver; delivering, by the portable drug delivery device, a dose of a drug stored in the drug payload to a body of a user based on first instructions received from the portable control device.

The drug delivery and drug cessation method may be further characterized, comprising: receiving, at the portable control device, second instructions comprising at least one of instructions based on user input, instructions based on preset dosages, or instructions from a healthcare professional via a computing device of the healthcare professional over a network, wherein the first instructions are based on the second instructions; and receiving, at the portable drug delivery device, the first instructions from the portable control device.

The disclosure teaches a drug delivery and drug cessation apparatus, comprising: a processor; and a non-transitory computer readable medium having stored thereon computer software comprising a set of instructions that, when executed by the processor, causes the apparatus to perform one or more functions, the set of instructions comprising: instructions to deliver, by a portable drug delivery device comprising a drug payload, a dosage delivery device, and a first wireless transceiver, a dose of a drug stored in the drug payload to a body of a user based on first instructions received from a portable control device comprising a second wireless transceiver, the portable control device being in wireless communication with the portable drug delivery device via the first wireless transceiver and the second wireless transceiver.

The drug delivery and drug cessation apparatus may be further characterized, wherein the set of instructions further comprises: instructions to receive a first set of dosage instructions comprising at least one of dosage instructions based on user input, dosage instructions based on preset dosages, or dosage instructions from a healthcare professional via a computing device of the healthcare professional over a network; and instructions to receive, at the portable drug delivery device, the first instructions from the portable control device.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The following examples are provided for illustrative purposes only and are not intended to limit the scope of the invention.

Example 1

Synthesis of nicotine meta-salicylate: 1.385 g m-salicylic acid (Sigma Aldrich) was dissolved in 25 ml of ethanol. 1.62 g nicotine was added drop wise at room temperature and mixed well for approx. 30 minutes. The solution was rotary evaporated slowly to reduce the volume to about 10 ml. Then 5 ml of ethyl acetate was added and stirred for 3-5 minutes. The solution was placed on dry ice for approx. 1.5 hours, which produced a sticky solid material. After evaporation of the solvent, 20 mL ethanol was added to dissolve the sticky solid and then evaporated. This recrystallization in known in the art for purifying crystals. Crystalline solid remained in the flask. The powder was removed from the flask and dried in a vacuum oven at 40° C. 2.6 grams were recovered (approx. 87% yield). The melting point of the solid was 125° C.

Example 2

Synthesis of nicotine meta-salicylate: Liquid Nicotine (Alfa Aesar, lot #10150504, purity 99%) and m-salicylic acid (3-hydrobenzoic acid, Sigma Aldrich, lot #STBB7747, purity 99%) were used to synthesize nicotine m-salicylate at a 1:1 nicotine:acid ratio. The following synthetic route leads to typical yields of 60-70% and purity 99.7%.

Sample synthesis:
1. Dissolved 0.03 moles of m-salicylic acid (~4.16 g) in 65 ml of ethanol 200 proof, and mixed well for about 20 min
2. Added 0.03 moles of liquid nicotine (~4.86 g) to above solution dropwise, mixed for 30-40 min on stir plate with periodic shaking. Seed crystals of nicotine m-salicylate were then added and the solution stirred for another 40 min, then placed on dry ice for about 40 min.
3. Filtered and washed nicotine m-salicylate with 100% acetone and let it air dry for ~20 min; to homogenize the salt, a mortar and pestle were used and then the salt was dried in a vacuum oven at 40° C. for 1 hour.
4. Salt was transferred into a scintillation vial and weighed. 6.0 g were recovered (~67% yield). The salt is a white powder with melting point of 125° C. Note that in the very first synthesis of this material (before there were seed crystals to utilize), after step 2 (dropwise addition of nicotine) the solution was rotary evaporated slowly to reduce to ~10 ml volume. Then 50 ml of ethyl acetate was added, mixed well, and the solution placed on dry ice. A sticky material resulted, which was further evaporated. 20 ml of ethanol was added, the solution placed again on dry ice, at which point crystallization occurred. The crystals were filtered, washed and dried under vacuum at 40° C.

Example 3

API Assessment

The nicotine m-salicylate raw material (API) was characterized with a number of analytical methods. The results prove that the nicotine m-salicylate as synthesized is highly pure.

Figure 7:
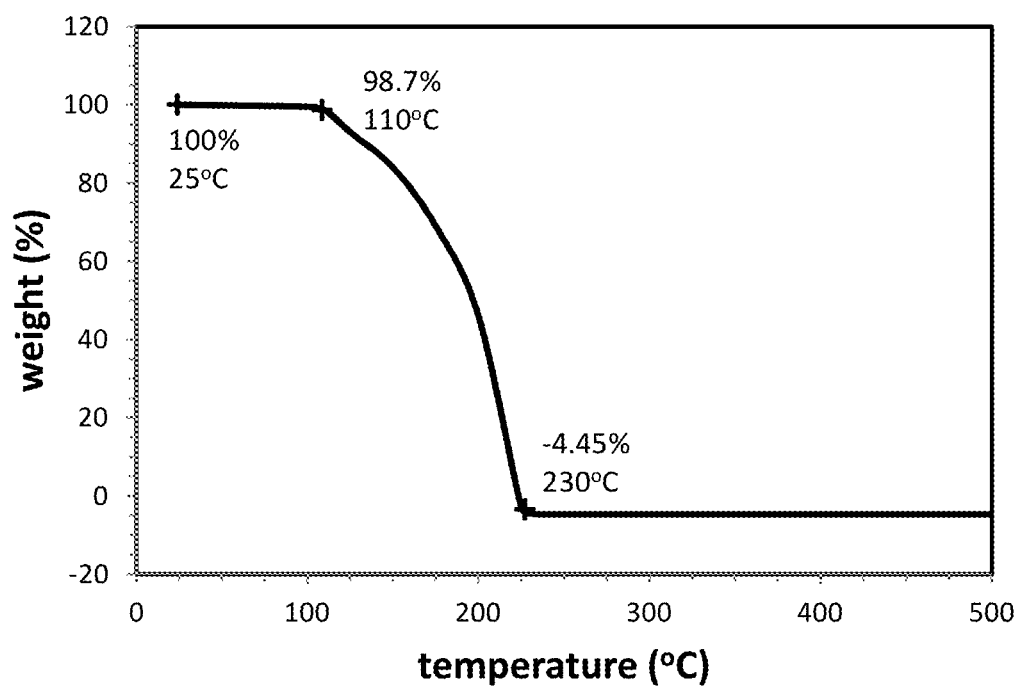
FIG. 7 shows thermogravimetric analysis. Scanning data from room temperature to 500° C., showing minimal charring of the acid after exposure to high temperatures.
Figure 8:
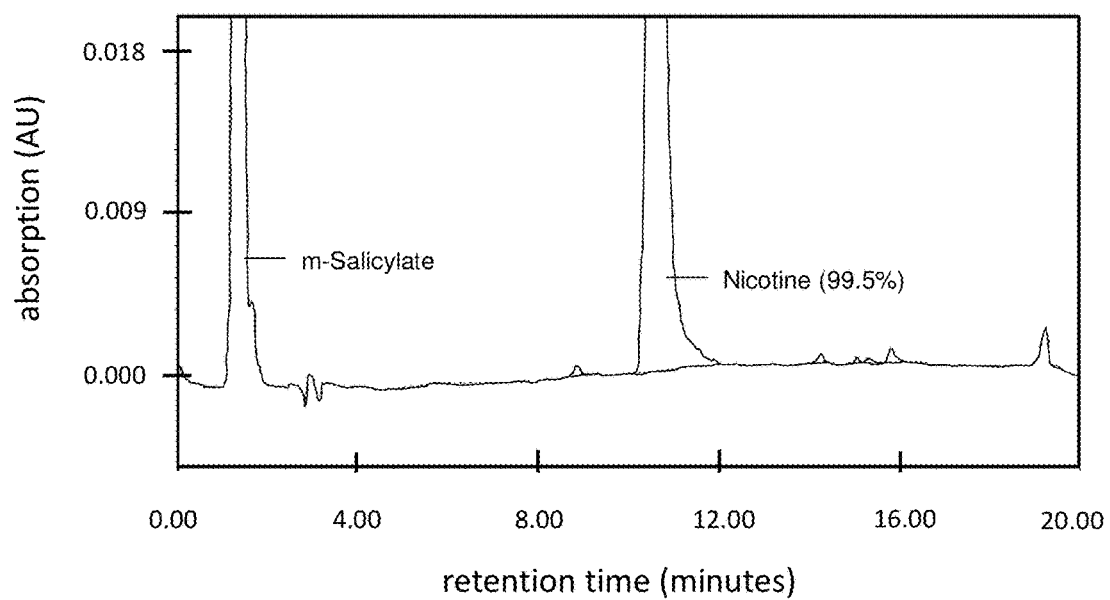
FIG. 8 shows a chromatogram of a typical sample run on the nicotine impurity method.
Figure 9:
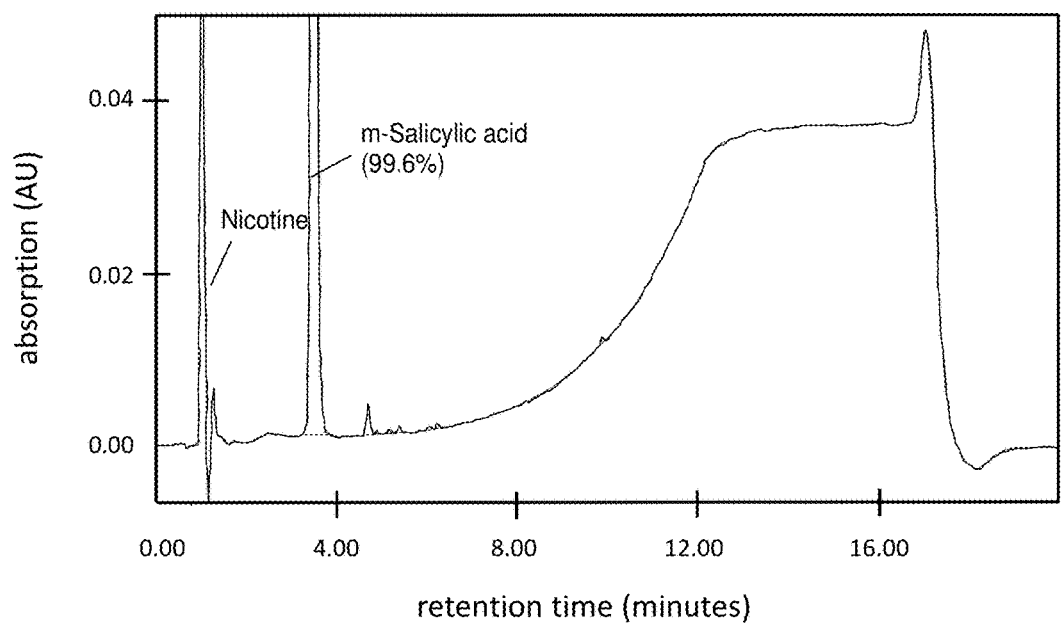
FIG. 9 shows a chromatogram of a typical sample run on the m-salicylate impurity method.

A typical calorimetric scan of nicotine m-salicylate powder is illustrated in FIG. 2. The melting point is 125° C. Thermogravimetric analysis on the powder was run in both scanning and isothermal modes. FIG. 7 shows the scanning data, from room temperature to 500° C. Note the flat baseline near (actually, slightly below) 0%, indicating little to no residue left behind. The pan was weighed before and after on an external balance, and the residual was only ~0.2%. This result suggests minimal charring of the acid after exposure to high temperatures. Isothermal data were also obtained on the API powder (~10 mg per run) at 40° C., 50° C., and 60° C. for periods of at least 3 days. In all cases, the mass change was essentially a linear decrease with time. A summary of the data, along with similar data obtained for various other nicotine salts, is detailed in Table 2. Nicotine meta-salicylate (top line) lost about 2-3× less nicotine than nicotine ortho-salicylate (second line). Most of the nicotine salts tested were less stable (lost more nicotine) than the m-salicylate salt.

TABLE 2

Nicotine mass loss observed during thermogravimetric analysis experiments on various nicotine salts

| Species | Nicotine Mass Loss (mcg/day) | | |
|---|---|---|---|
| | 40° C. | 50° C. | 60° C. |
| Nicotine m-salicylate | 5 | 19 | 107 |
| Nicotine o-salicylate | 15 | 48 | 178 |
| Nicotine bitartrate | 1 | 3 | 10 |
| Nicotine monofumarate | 7 | 39 | 219 |

TABLE 2-continued

Nicotine mass loss observed during thermogravimetric analysis experiments on various nicotine salts

| Species | Nicotine Mass Loss (mcg/day) | | |
|---|---|---|---|
| | 40° C. | 50° C. | 60° C. |
| Nicotine bifumarate | 12 | 66 | 305 |
| Nicotine bidimethylmalonate | 4 | 14 | 53 |
| Nicotine monodimethylmalonate | 51 | 374 | 2707 |

Example 4

Solubility

Solubility limit tests were performed on nicotine m-salicylate in a number of relevant solvents. Results are compiled in Table 2. The approximate saturation limits are in units of mg nicotine equivalent per mL of solvent. Note the solubility of nicotine m-salicylate is low in pure acetonitrile (~10 mg/mL) and acetone (<10 mg/mL). Nicotine m-salicylate is most soluble in solvent systems containing methanol. However, the analytical methods developed for detecting impurities related to the m-salicylate use 236 nm as the detection wavelength. Methanol has high absorbance in this range and can therefore interfere with the analytes of interest. Acetonitrile, on the other hand, has low background absorbance in this wavelength range and is therefore ideal for use. To counter the poor solubility, extractions use mixtures of water and acetonitrile.

TABLE 3

Approximate Solubility Limits of Nicotine m-salicylate in Various Solvents

| Solvent | Saturation point (mg nicotine/mL) |
|---|---|
| Acetonitrile | 9 |
| Ethanol | 33 |
| Water | 58 |
| 50/50 acetonitrile/water | 64 |
| 80/20 methanol/water | 118 |
| Acetone | <<10 |
| Methanol | 103 |

Example 5

Nicotine Coating Development

Spray coating is one of the key manufacturing steps for producing the drug films that lead to condensation aerosols. Spray coating of nicotine m-salicylate was done with solutions of ~75 mg/mL in methanol. Acetone was also tried, but the solubility was limited. Typical spray coating parameters were 1.3 W (Broadband Ultrasonic Generator power), solution flow rate 10-12 mL/hr, coating table speed 25 mm/s, and air pressure 1-1.5 psi. Higher flow rates tend to lead to visibly more heterogeneous coatings. Intra-array relative standard deviations were often in the 2-3% range, though inter-array variability was higher (likely due to overspray onto neighboring arrays). Crystallization of the coated films is preferable, and usually occurs quite readily after manual seeding of the spray nozzle.

Coatings were made such that the 200 μg nicotine equivalent dose covers one surface of the foil, in a 9×2 mm area.

This is equivalent to a film thickness of approximately 20 µm. Lower dosages were coated over the same surface area, for the characterization studies described below. However, as the mechanical stability of the highest dose was found to be acceptable, and the evaporative loss is less for thicker films, the disclosure teaches coating at the 20 µm thickness. New spray coating masks have been made to produce such films, at doses of 25, 50, and 100 µg nicotine equivalent.

Example 6

Analytical Method Development

Figure 10:
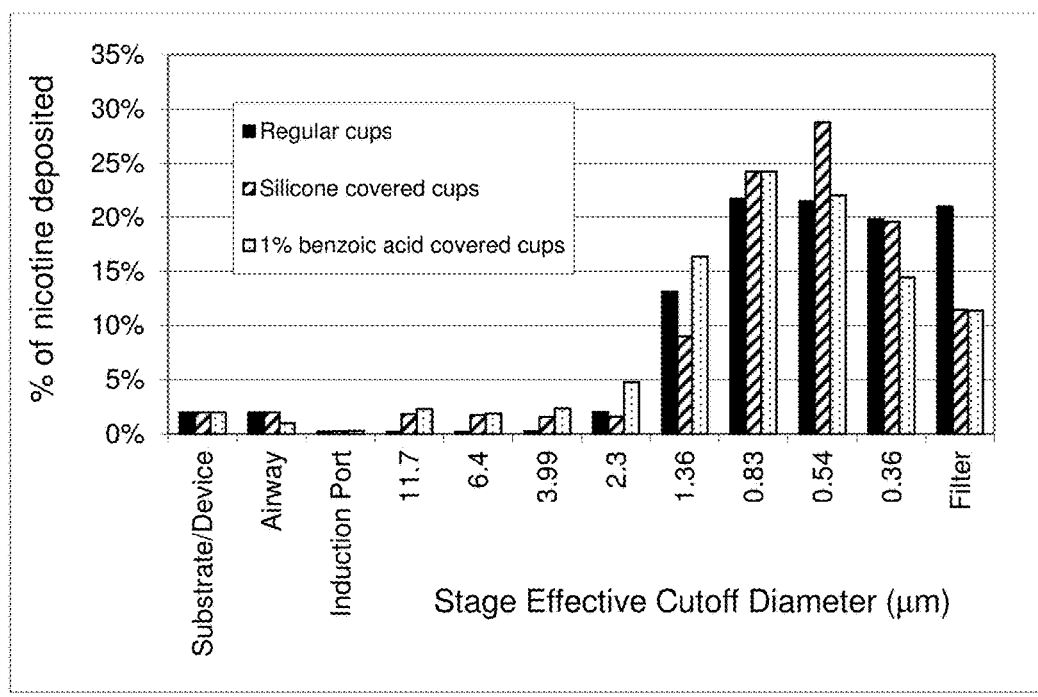
FIG. 10 shows the particle size distribution amongst the various impactor stages.

In conjunction with the drug product development of nicotine m-salicylate, a number of analytical methods have been derived to assist with the quantitative and qualitative (purity) assessment of the API and the aerosol.

Nicotine quantitative: This isocratic assay uses a Gemini C18, 50×3 0 mm, 3 μm column, 0.1% ammonium hydroxide in water/acetonitrile mobile phase with flow rate of 0.6 mL/min and detection at 245 nm. The total run time for this method is 3 minutes. This procedure is applicable for determining nicotine concentrations in the range of 8 to 200 μg/mL for low quant and 100 to 600 μg/mL for high quant in nicotine salts. It is not intended for the measurement of impurities or degradants of nicotine.

M-salicylic acid quantitative method: This isocratic assay uses a Luna, C18, 3 μm, 75×4.6 mm column, 0.1% trifluoroacetic acid (TFA) in water/acetonitrile mobile phase with flow rate of 1.0 mL/min and detection at 248 nm. The total run time for this method is 3.5 minutes. This procedure is applicable for determining m-salicylic acid concentrations in the range of 20 to 600 μg/mL. It is not intended for the measurement of impurities or degradants of m-salicylic acid.

Nicotine purity method: This reverse phase HPLC method applies a gradient flow with a mobile phase composed of 0.1% (v/v) ammonium hydroxide in water/acetonitrile at a flow rate of 0.8 mL/min, and uses a Gemini RP18, 150×4.6 mm, 3 μm column, and UV detection at 260 nm. The total run time for this method is 20 minutes. This procedure is applicable for determining nicotine concentrations and the nicotine related impurities in a nicotine concentration range of 300 to 500 μg/mL. It is for the determination of the total nicotine-related impurities in nicotine m-salicylate.

M-salicylic acid purity method (AARD-020-049): This reverse phase HPLC method applies a gradient flow with a mobile phase composed of 0.1% (v/v) trifluoroacetic acid (TFA) in water/acetonitrile at a flow rate of 0.8 mL/min, and uses a Gemini C18, 150×3.0 mm, 5 μm column, and UV detection at 236 nm. The total run time for this method is 20 minutes. This procedure is applicable for determining m-salicylate concentrations and the m-salicylate related impurities in an m-salicylate concentration range of 300 to 500 μg/mL. It is for the determination of the total m-salicylic acid-related impurities in nicotine m-salicylate.

Example 7

EMD Characterization

Emitted Dose and Mass Balance

Emitted Dose and Mass Balance: Due to the volatile nature of nicotine, a thorough collection of nicotine particles and vapors proved to be extremely challenging. Many iterations of emitted dose testing were performed to find the optimal collection method that enabled 100% mass balance.

Ultimately, a 76 mm diameter glass fiber filter (1.0 um pore size, type A/E), housed in the NGI filter holder, was found to provide the optimal recovery of both nicotine and the m-salicylate. Possibly the nicotine salicylate salts require a relatively slow face velocity across the filter for adequate collection. Emitted dose experiments were conducted using a switch box with external power supply to provide the energy to heat up the foils and vaporize the drug. Up to 3 foils can be fired into one filter without negatively impacting recovery. (Actuating more foils into one filter decreases aerosol recovery, possibly due to the volatility of free base nicotine from the extra air flow across the collection filter.) The switch box was set to provide 3.7 volts/4.0 amps for 0.5 seconds. Airflow rate was set at 28.3 LPM. The captured drug vapors were then extracted from the filter using up to 10 mL of 50% (v/v) acetonitrile in water and sonicated for 10 minutes. Filter fibers are pelleted out by centrifugation before the analyte is prepared for HPLC analysis.

The average nicotine emitted dose from foils coated with 200 μg nicotine was 99.5% of coated dose (6.8% SD) while the average m-salicylate recovery was 101.8% compared to coated dose (6.3% SD). Both had minimal deposition/residual on the foils and airway housing. Additionally, an analysis of the nicotine to counter-ion molar ratios for both the coated dose and emitted dose results show that the 1:1 relationship is conserved during the vaporization and capture process.

Aerosol Purity

Aerosols were captured with the emitted dose procedure, with extractions carried out in 50/50 acetonitrile/water. The purity of the aerosol is dictated by both the nicotine and the salicylate entities. The nicotine moiety appears to vaporize almost completely intact, with minimal (≤0.5%) degradation. Small amounts of myosmine were detected. FIG. 8 shows a chromatogram of a typical sample run on the nicotine impurity method.

The challenge of a number of the nicotine salts, such as the tartrate, has been the decomposition of the acid. What complicates the situation further is the analytical challenge in observing their degradation byproducts, since these carboxylic acids are small molecules with minimal UV absorption. The m-salicylate, fortunately, has some advantages in this regard. We were able to develop an HPLC method for screening degradation of m-salicylate. Minimal degradation products from m-salicylic acid have been detected (≤0.5%). FIG. 9 shows a chromatogram of a typical sample run on the m-salicylate impurity method.

An additional concern of the m-salicylic acid was the possible formation of phenol. Phenol has been detected as a decomposition product of nicotine o-salicylate at levels of ~0.1-0.5%. While phenol is a relatively ubiquitous molecule, there are some reports of genotoxicity and irritation.

Using a sensitive LC method for phenol detection, this method did not observe phenol in nicotine m-salicylate aerosols. Given the sensitivity of the method, we can estimate a maximum content of about 0.013% phenol in the nicotine m-salicylate aerosols. A complementary approach to evaluating aerosol purity is calculating the mass balance, i.e., comparing the coated dose amount to the emitted dose plus the residual amounts of nicotine and counterion. Comparing the amounts and ratio of nicotine and m-salicylic acid in the coated vs. emitted+residual drug shows that unlike the tremendous disparity seen in salts such as nicotine bitartrate, the mass balance of both entities is about 100% and the ratio in the aerosol is consistent with that of the coated dose.

Aerosol Particle Size Results

Particle size experiments were conducted on the Next Generation Impactor (NGI). Airflow rate was set at 30 LPM. Foil arrays coated with 200 μg of nicotine equivalent (about 370 g total of nicotine m-salicylate) were vaporized using an EMD dose cartridge switch box at settings similar to the emitted dose experiments. Four to eleven foils were vaporized into each NGI set and cups were assayed with 4 mL of 50% (v/v) acetonitrile in water. Initially, bare NGI cups resulted in low MMAD values, with an average of 0.7 μm. Silicone was then sprayed onto the cups to reduce the bounce effects often seen with particle size experiments. Silicone sprayed cups had no effect on MMAD, though mass balance improved slightly, increasing nicotine recovery from 76% of coated dose for bare cups to 89% on silicone cups. The NGI cups were then coated with a thin layer of 1% (w/v) benzoic acid to reduce bounce and nicotine volatility. An aliquot of the solution was pipetted into each cup, and the cups were swirled to expedite surface coverage. The presence of benzoic acid increased the MMAD to 0.9 um, while nicotine recovery improved to 93% of coated dose. FIG. 10 shows the particle size distribution amongst the various impactor stages for these setups.

Figure 11:
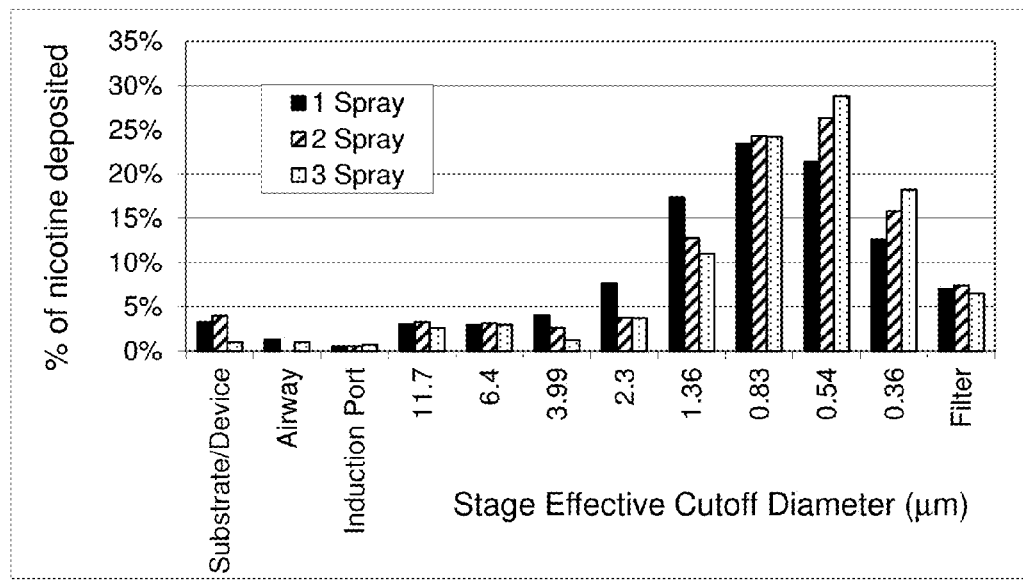
FIG. 11 shows particle size distributions.
Figure 12:
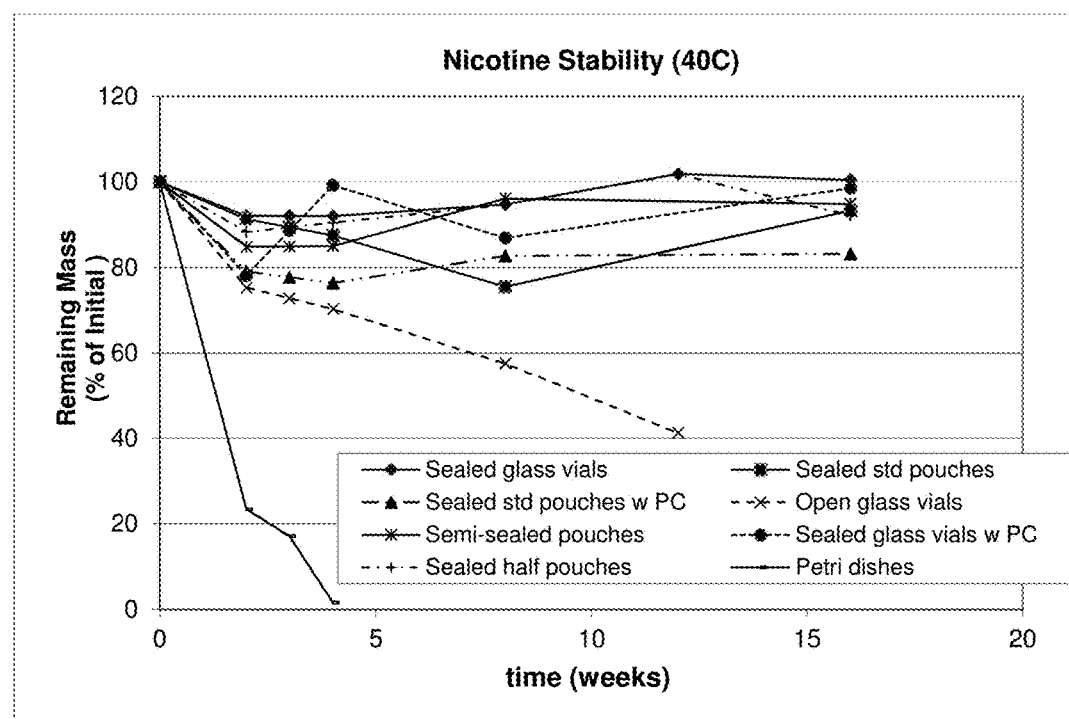
FIG. 12 shows nicotine mass loss over time.
Figure 13:
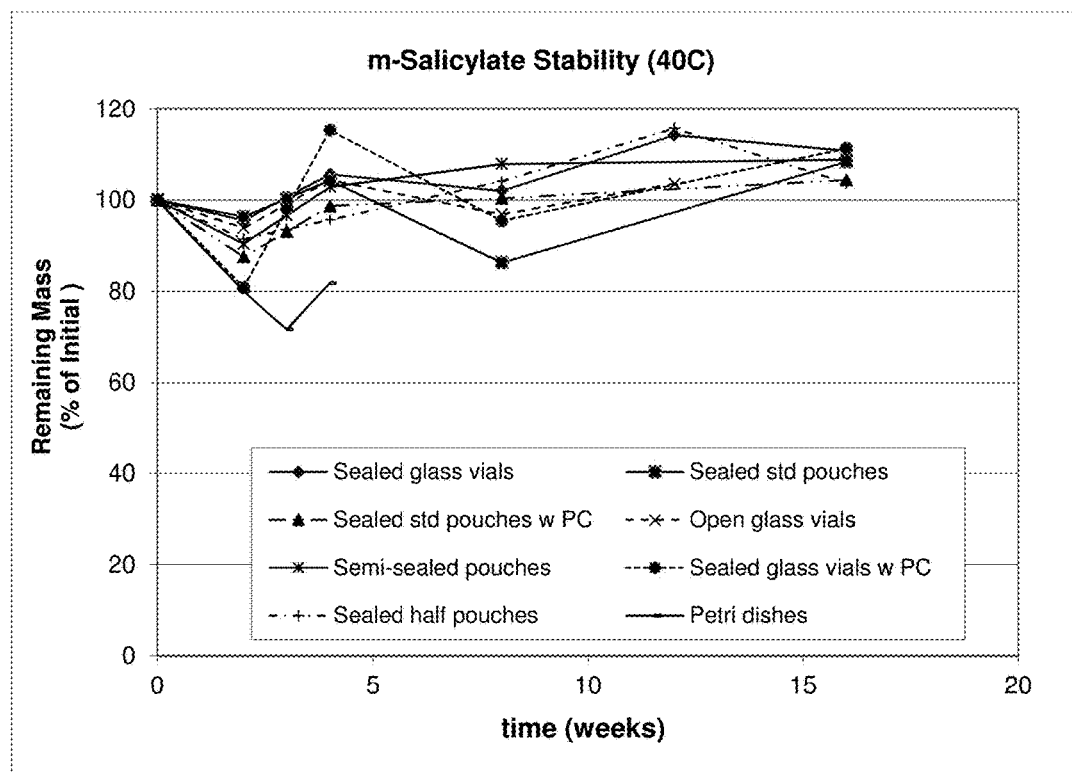
FIG. 13 shows m-salicylic acid mass loss over time.

Further experiments to determine effects of benzoic acid coating uniformity and thickness (by varying number of sprays from a spray bottle) showed minimal difference to the MMAD, with results ranging from 0.8 to 1.0 μm. See FIG. 11. Particle size is about 1 μm, or just slightly less, which should be appropriate for pulmonary deposition. It is likely that the nicotine m-salicylate aerosols would grow somewhat in the humid (nearly 100% RH) atmosphere inside the respiratory tract.

Example 8

Stability

The innate volatility of free base nicotine can be greatly altered once bound to a counterion acid. The stability of nicotine in the resulting salt form can vary widely, ultimately impacting its desirability for commercial consideration. Certain packaging configurations can mitigate nicotine loss. Previous experimental results suggested that nicotine loss is halted once the equilibrium vapor pressure of nicotine is reached. Decreasing the equilibrium vapor pressure point is believed to minimize the total nicotine loss. For this study, different packaging configurations were tested to investigate the following variables: container material, presence of adjuncts, and total volume of space. Container materials consisted of either glass or multi-laminate foil pouches. Glass is impermeable to vapors. Once the total volume of the glass container is flooded with nicotine vapors and any surface adsorption occurs, equilibrium is reached and no additional loss of nicotine should be observed. Though foil is also impermeable, the inner surface of the pouch is lined with an ethylene acid copolymer that promotes vapor absorbency. The copolymer should lead to greater nicotine loss within a pouch than a glass vial of the same total volume.

The presence of adjuncts, such as a drug cartridge housing, is a likely scenario for the final commercial product. The composition of the adjunct will affect equilibrium vapor pressure point if it preferentially absorbs vapors. For this study, a polycarbonate adjunct with a surface area of ~150 $cm^2$ was introduced to the glass vial and pouch scenarios. Finally, the total packaging volume was examined The smaller the available space, the sooner the equilibrium pressure can be reached. Open containers represent the worst case scenario, as the infinite space means that the equilibrium pressure can never be achieved. To set up the experiment, screening foils were spray coated with a 1×2cm footprint of nicotine m-salicylate to a thickness of ~11 ug nicotine/$mm^2$ (equivalent to a coated dose of 200 ug nicotine equivalent on an EMD foil). After a few random screening foils were assayed for initial time point coated dose, the remaining foils were placed in one of the following containers:

Capped glass vial (~40 mL volume)
Heat-sealed standard pouch (~133 mm×87 mm)
Heat-sealed standard pouch, stored with polycarbonate material (~150 $cm^2$ surface area)
Uncapped glass vial (same vial as first bullet)
Binder-clipped (semi-sealed) standard pouch (~133 mm×87 mm)
Capped glass vial, stored with polycarbonate
Heat-sealed half pouch (~69 mm×87 mm)
Uncovered Petri dish The packaged screening foils were stored at either 40° C. (oven) or 25° C. (laboratory cabinet), without relative humidity control. At pre-determined time points, three foils from each condition were washed with 5 mL of 50% v/v acetonitrile in water and analyzed on the HPLC for nicotine and m-salicylate content.

Figure 14:
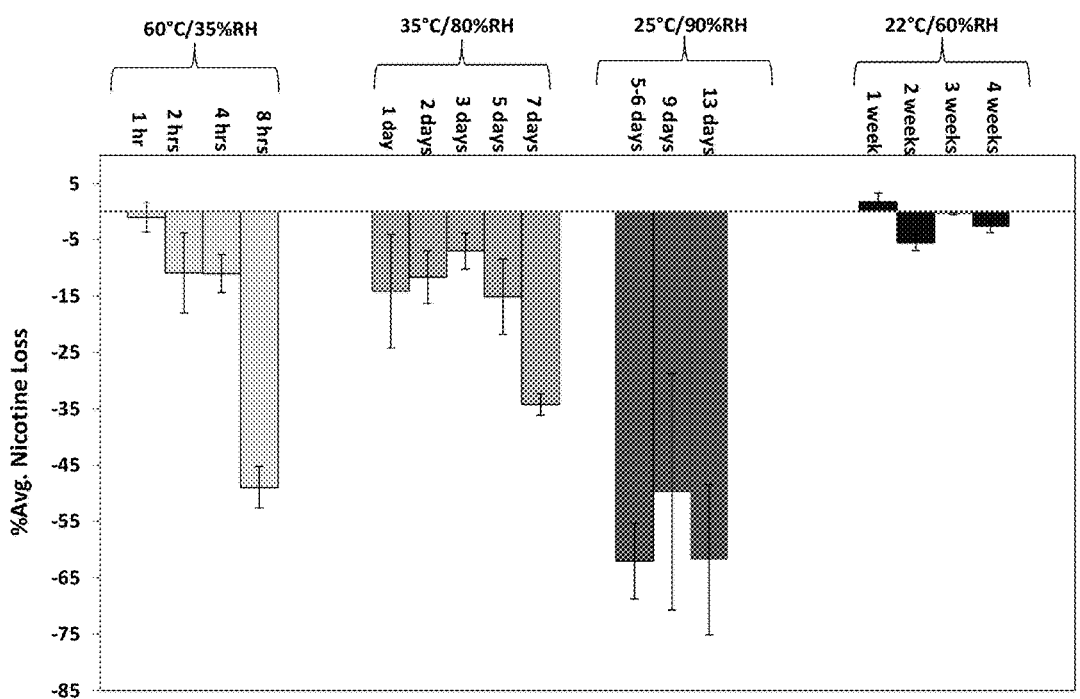
FIG. 14 shows unpouched stability summary
Figure 15:
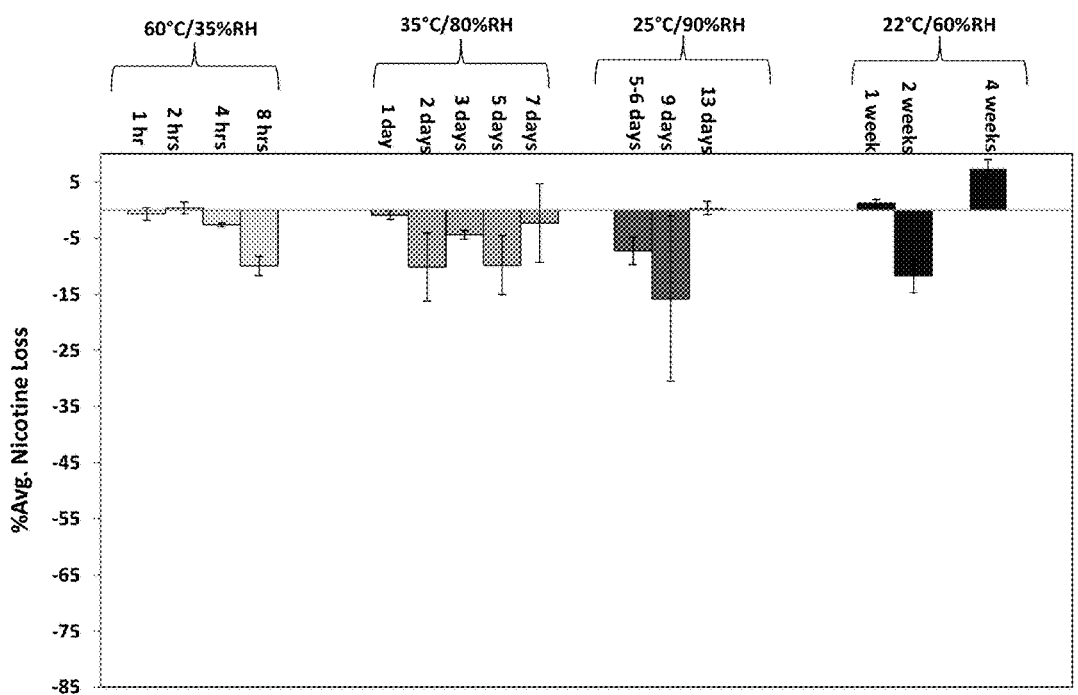
FIG. 15 shows unpouched stability summary

The results for the 40° C. samples are presented in FIG. 14 and FIG. 15. Only two conditions exhibit continued loss of nicotine throughout storage duration: the open glass vial and the uncovered Petri dish. All other conditions in which the packaging was sealed demonstrated a stabilization of nicotine volatility after an initial loss.

The sealed standard sized pouches containing polycarbonate material appear to be the worst of the stabilized nicotine conditions (loss of ~20% nicotine content). The spray coated nicotine salt was exposed to the copolymer layer and the polycarbonate adjunct and the total volume was twice that of the half sized pouch. All other stabilized nicotine conditions lost ≤10% of its nicotine content.

The Petri dish condition had the most rapid nicotine loss due to its storage configuration. The entire surface of the spray coated foil was continually exposed to the outside environment. Meanwhile, the foils in the open glass vials were stored upright in a narrow vial with only a small diameter of the space exposed to the outside, thereby reducing the rate of loss.

The m-salicylic acid appears to be very stable, regardless of packaging configuration. The Petri dish condition is the worst case scenario due to its maximal exposure to the outside environment. However, after four weeks of storage at 40° C. with minimal humidity, the m-salicylate content remained at ~80% of initial. Otherwise, the stability results are in the range of about 100-110% of initial for all other configurations after 16 weeks of storage.

The results for the samples stored at 25° C. are especially promising. Nicotine loss for all conditions up to 18 weeks of storage were within 7% of initial, except for the Petri dish condition (13% loss of nicotine content at 18 weeks). The m-salicylic acid content was stable for all eight conditions.

Loss of nicotine and m-salicylic acid due to volatility and hygroscopic effects: Nicotine salts can suffer volatility issues and can also be quite hygroscopic. For instance, nicotine sulfate absorbs water so readily that it is shipped in aqueous solution. Hygroscopic effects on nicotine m-salicylate were evaluated for 2 doses at two conditions, 22° C./44% RH (ambient condition) and 40° C./75% RH. According to the Antoine equation for water, 40° C./75% RH translates to supersaturated humidity at 22° C. Each coated EMD array was placed flat on a Petri dish (without a cover) which was then stored at either 22° C./44% RH or 40° C./75% RH. At each time point, at least 4 random individual foils were removed from the array and each foil was extracted with 1.5 ml of 50/50 ACN/water for coated dose determination.

Overall nicotine results for the 40-μg/foil and 170-μg/foil conditions are summarized as follows. See FIG. 14. For the 40 μg/foil dose, coated films were relatively stable (defined as not more than 20% loss) for up to 4 hours at 60° C./35% RH, 5 days at 35° C./80% RH, and 4 weeks at 22° C./60% RH. For the 170 μg/foil dose, coated films are stable for at least 8 hours at 60° C./35% RH, 7 days at 35° C./80% RH, 13 days at 25° C./90% RH and 4 weeks at 22° C./60% RH. Stability results demonstrate that across all stability conditions, the thicker coated films (170 μg/foil) are significantly more stable than the thinner coated films (40 μg/foil). M-salicylic acid results for 40 μg/foil and 170 μg/foil are summarized as follows. See FIG. 15. M-salicylic acid seemed to be relatively stable for all conditions except for the 40 μg/foil dose at 25° C./90% RH. Fortunately, this issue can be mitigated by increasing the coated film thickness.

Mechanical Stability

Fragility of the spray coating was tested using two foil arrays coated with ~200 μg of nicotine per foil (~11 μg nicotine/mm$^2$, which is about a 21 μm thick film of nicotine m-salicylate). Five foils from each array were assayed for pre-drop coated dose. Each foil array was then placed into a dose cartridge, sealed into a plastic tube, and dropped 3 times onto the floor from a height of about 1 meter. Five additional foils from each array were assayed for the post-drop coated dose. The intra-foil array coated dose was found to be 0.1 and 1.4% higher for the post-drop compared to pre-drop, with an average of ~0.8%. In these circumstances, these differences are insignificant and show that even the 200 μg nicotine equivalent coating of nicotine m-salicylate on the EMD foils are mechanically stable.

TABLE 1

Results of Mechanical Stability Test

| Drug Film thickness (μm)* | Test condition | Nicotine coated dose (average ± 1 standard deviation) | M-salicylate coated dose (average ± 1 standard deviation) |
|---|---|---|---|
| 29 | Pre-drop | 275 ± 3 | 247 ± 1 |
|  | Post-drop | 277 ± 3 | 244 ± 3 |
| 37 | Pre-drop | 347 ± 6 | 311 ± 0 |
|  | Post-drop | 335 ± 6 | 299 ± 7 |

*Assuming unit density (1 g/cm$^3$)

In a follow-up study, we studied the effect of thickness on the mechanical integrity of the film. In this experiment, three foils from an array were assayed for pre-drop coated dose. Each foil array was then placed into a dose cartridge, sealed into a plastic tube, and dropped 5 times onto the floor from a height of about 1 meter. Three foils from each array were then assayed for the post-drop coated dose. The data indicate that film thicknesses corresponding to 350 μg nicotine (~37 μm thick) begin to show signs of fragility—flaking off of the drug. The drug was not lost after dropping of films of ~29 μm thickness. Therefore, for mechanical purposes, nicotine m-salicylate film thicknesses should not exceed approximately 30 microns.

Example 9

Devices

Figure 16:
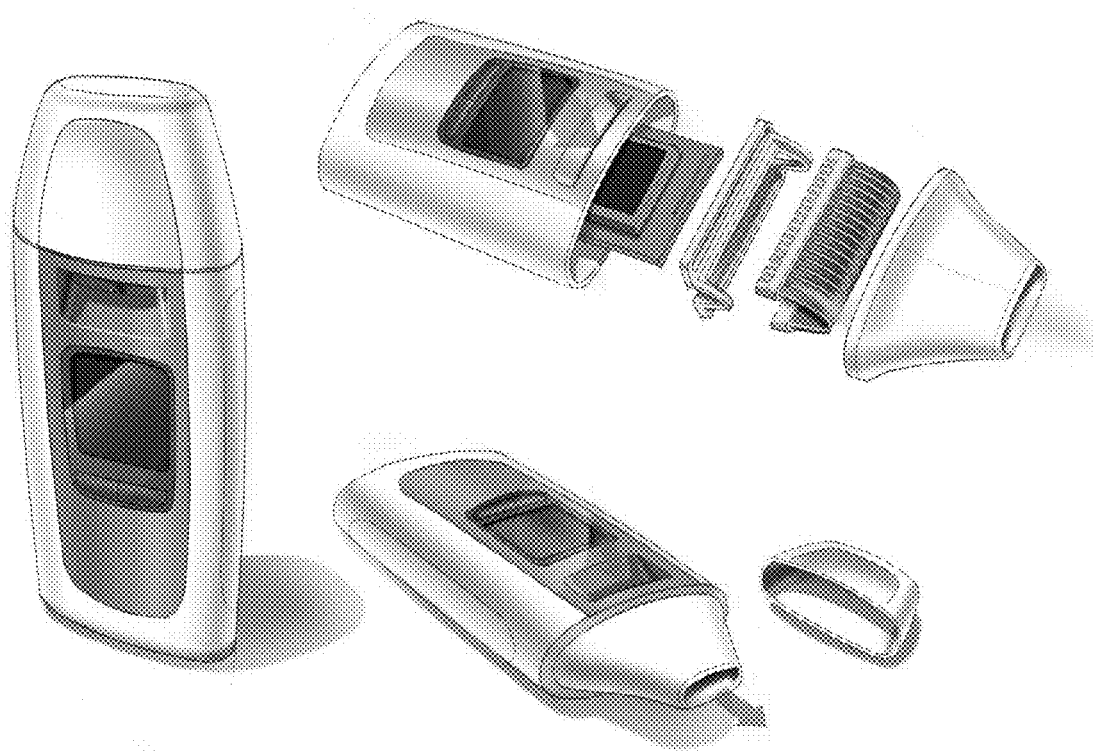
FIG. 16 Nicotine device 1.

Device 1: The basic design as shown in FIG. 16 has been tested in the Electric Multi Dose (EMD) platform. Efficient foil packaging translates to a large number of doses. The foils are readily coated via spray process.

Figure 17:
FIG. 17 Nicotine device 2.

Device 2: See FIG. 17. The doses are in the forms of small coils, wound from a solid, resistive wire such as Ni-Chrome. The coils are connected in such a way that the coil furthest from the mouthpiece offers the path of least resistance. The wire diameter is selected such that a short current burst will heat up that coil first, and subsequently blow the fuse connection point (red dot). At that point, the coil is spent and no longer connected to the circuit. On the next heating cycle, the next coil presents the path of least resistance, so it becomes the next dose. The cycle continues until all the doses are consumed. Fail-safe design of single dose can be implemented without software. Can be a disposable unit. Form factor can be similar to a cigarette. Can leverage from wire bonding technology for coil attachment. Can be converted to software control of heating elements.

Figure 18:
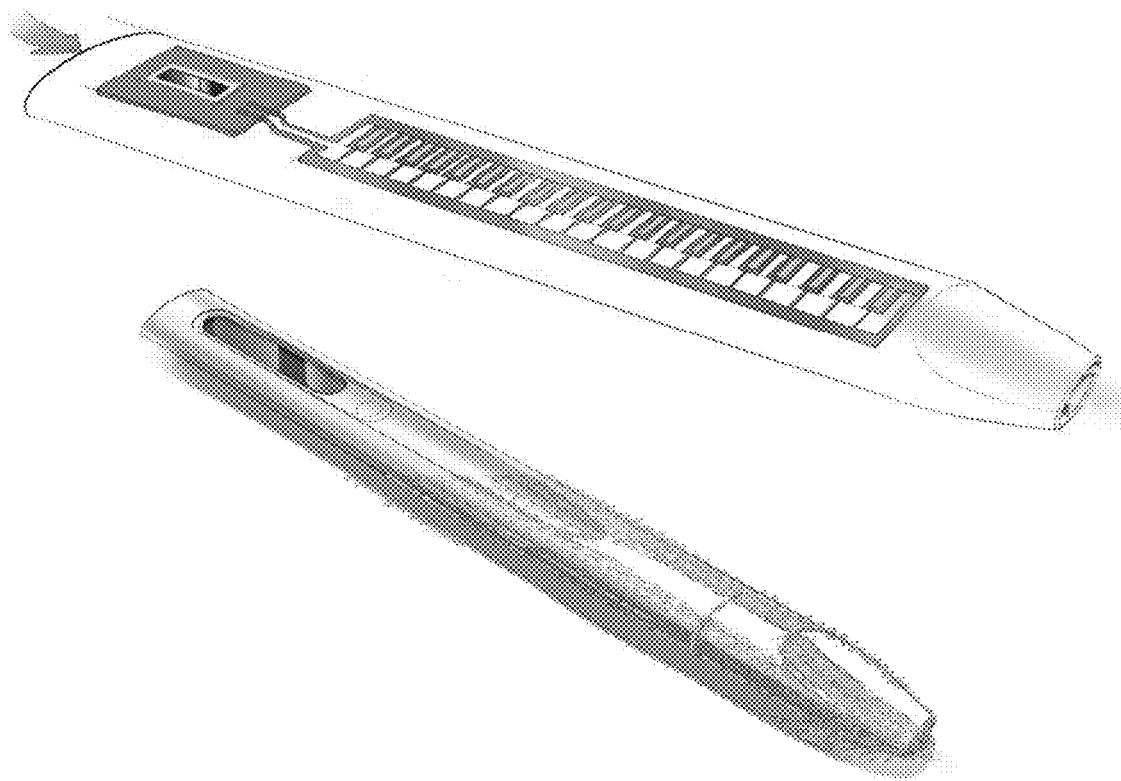
FIG. 18 Nicotine device 3.

Device 3: See FIG. 18. The device relies on the same fusing approach as Device 2 but it employs foils rather than coils wound from wire. A fail-safe design of single dose can be implemented without software. The device may be a disposable unit. The form factor is close to a cigarette. The is an efficient area layout which translates to higher number of doses per device. There are only two connection points. Execution of reduced area for fusing is readily accomplished with the foil. The device can easily be converted to software controlled heating elements. Flat foils will be readily coated via a spray process.

Figure 19:
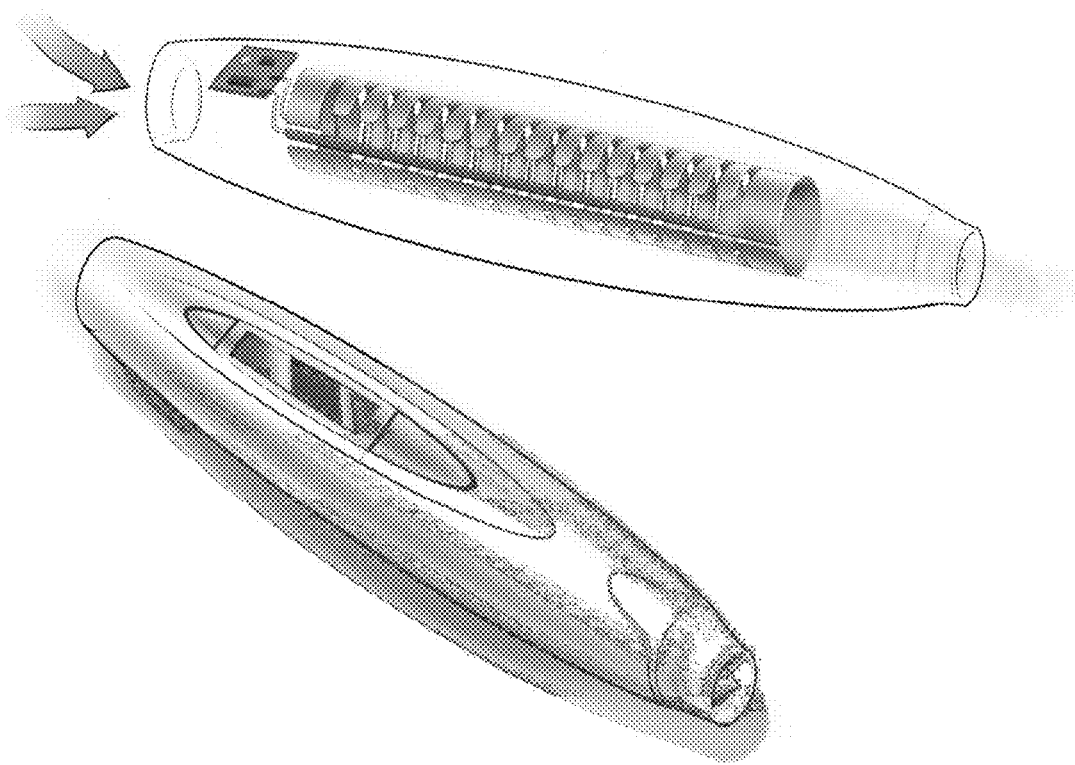
FIG. 19 Nicotine device 4.

Device 4: See FIG. 19. This device relies on the same fusing approach as in Devices 2 and 3. It employs foils that are wrapped in a tubular form to allow for a cigarette like form factor.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A drug supply article comprising:
   a heat-conductive substrate having an impermeable surface;
   a nicotine composition comprising nicotine meta-salicylate coated on at least a portion of the surface in the form of a film having a thickness; and
   a heat source operable to supply heat to the substrate at a rate that achieves a temperature sufficient to vaporize all or a portion of the coated nicotine composition within a period of 2 seconds;
   wherein the vaporized nicotine composition comprises an effective amount of the nicotine;
   wherein the film has a thickness between 0.05 and 30 microns.

2. The drug supply article of claim 1, wherein the nicotine composition comprises a pharmaceutically acceptable excipient.

3. The drug supply article of claim 1, wherein the film thickness is between 0.1 and 30 microns.

* * * * *